United States Patent [19]
Yoshida et al.

[11] Patent Number: 6,087,010
[45] Date of Patent: Jul. 11, 2000

[54] FLUORINE-CONTAINING POLYFUNCTIONAL (METH) ACRYLATE COMPOSITION LOW REFRACTIVITY MATERIAL AND REFLECTION REDUCING FILM

[75] Inventors: Tatsurou Yoshida; Yasuhiro Kimura, both of Tsukuba; Kenji Watanabe, Makabemachi; Tomoyuki Ikeda; Tetsuya Itoh, both of Tsukuba; Yoshitaka Goto, Yawaramura, all of Japan

[73] Assignee: NOF Corporation, Tokyo, Japan

[21] Appl. No.: 09/011,812

[22] PCT Filed: Jun. 9, 1997

[86] PCT No.: PCT/JP97/01952

§ 371 Date: Feb. 9, 1998

§ 102(e) Date: Feb. 9, 1998

[87] PCT Pub. No.: WO97/47585

PCT Pub. Date: Dec. 18, 1997

[30] Foreign Application Priority Data

| Jun. 10, 1996 | [JP] | Japan | 8-147139 |
| Sep. 17, 1996 | [JP] | Japan | 8-244963 |
| Nov. 5, 1996 | [JP] | Japan | 8-292640 |
| Nov. 8, 1996 | [JP] | Japan | 8-296509 |
| Jun. 6, 1997 | [TW] | Taiwan | 86107841 |
| Jun. 10, 1997 | [JP] | Japan | 9-152239 |
| Sep. 16, 1997 | [JP] | Japan | 9-251083 |

[51] Int. Cl.[7] ............... B32B 27/00; C08F 18/20; C07C 69/66; C07C 69/52

[52] U.S. Cl. ............... 428/421; 428/422; 526/245; 524/544; 560/185; 560/197; 560/205; 560/223

[58] Field of Search ............... 560/205, 223, 560/183, 185, 193, 197; 526/245, 292.1, 292.3, 292.4, 318, 318.2, 318.43, 318.44, 320, 321, 322, 323, 237; 428/520, 480, 422, 421; 524/700, 544

[56] References Cited

U.S. PATENT DOCUMENTS

| 3,968,309 | 7/1976 | Matsuo et al. | 428/409 |
| 4,007,322 | 2/1977 | House | 526/292 |
| 4,273,802 | 6/1981 | Kamada et al. | 427/54.1 |
| 5,024,507 | 6/1991 | Minns et al. | 350/96.34 |
| 5,238,974 | 8/1993 | Yamamoto et al. | 522/75 |

FOREIGN PATENT DOCUMENTS 62-199643  9/1987  Japan.

*Primary Examiner*—Paul Thibodeau
*Assistant Examiner*—Kevin R Kruer
*Attorney, Agent, or Firm*—Darby & Darby

[57] ABSTRACT

Fluorine-containing polyfunctional (meth)acrylate represented by the formula (1), as well as a composition, a low refractivity material and a reflection reducing film in which the (meth)acrylate is utilized:

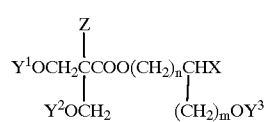

(1)

wherein X stands for a fluoroalkyl group of C1–14 having 3 or more F, or a fluorocycloalkyl group of C3–14 having 4 or more F; $Y^1$, $Y^2$, and $Y^3$ stand for H, an acryloyl group or a methacryloyl group, and at least two of $Y^1$, $Y^2$, and $Y^3$ stand for an acryloyl group or a methacryloyl group; Z stands for H or an alkyl group of C1–3; and n and m is an integer of 0 or 1, and n+m=1.

10 Claims, 8 Drawing Sheets

FLUORINE-CONTAINING POLYFUNCTIONAL (METH) ACRYLATE COMPOSITION LOW REFRACTIVITY MATERIAL AND REFLECTION REDUCING FILM

This application is a national stage application for PCT JP97/01952 filed Jun. 9, 1997 and entitled to the priority the Japanese applications 8-147139, 8-244963, 8-292640, 8-296509, filed Jun. 10, 1996, Sep. 17, 1996, Nov. 5, 1996, and Nov. 8, 1996, respectively, the priority of which is claimed.

BACKGROUND ART

The present invention relates to novel fluorine-containing polyfunctional (meth)acrylate; compositions which can be used as a starting material for preparing a low refractivity material having both high surface hardness and low refractive index and being able to be applied to the surface of various kinds of substrates; a low refractivity material prepared by curing the composition by polymerization; and a reflection reducing film provided with the low refractivity material.

Compounds having a fluorine atom have low refractive index, and can be used for antireflection films or a clad material for optical fibers. In either applications, the lower the refractive index of the compound, the better the property of the products. There are proposed, for example, application of fluorine-containing (meth)acrylate polymers, copolymers of fluorine-containing (meth)acrylate with other monomers, tetrafluoroethylene polymers, copolymers of vinylidene fluoride and tetrafluoroethylene, or copolymers of vinylidene fluoride and hexafluoropropylene to optical fibers (Japanese Laid-open Patent Application Nos. 59-84203, 59-84204, 59-98116, 59-147011, and 59-204002).

Recently, there has attempted to apply solvent-soluble fluorine-containing polymers having low refractive index such as fluoroalkyl acrylate polymers, fluoroalkyl methacrylate polymers, or amorphous perfluoro resins such as CYTOP (trade name) manufactured by ASAHI GLASS COMPANY, or TEFRON AF (trade name) manufactured by E.I. du Pont de Nemours and Co. to reflection reducing films (Japanese Laid-open Patent Application Nos. 64-16873, 1-149808, and 6-115023).

These fluorine-containing resins, however, are non-cross-linked resins, and thus have low surface hardness after curing, inferior abrasion resistance, and insufficient adhesion.

For the purpose of improving the surface hardness, there has been proposed cross-linked polymers prepared from a suitable mixture of fluorine-containing monofunctional (meth)acrylate or fluorine-containing bifunctional (meth)acrylate and polyfunctional (meth)acrylate not containing fluorine (Japanese Laid-open Patent Application Nos. 58-105943, 62-199643, and 62-250047). The refractive index and the surface hardness of these cross-linked polymers may be adjusted to some extent by suitably selecting the content of fluorine in the fluorine-containing (meth)acrylate, or the mixing ratio of the fluorine-containing (meth)acrylate to the polyfunctional (meth)acrylate not containing fluorine. However, the fluorine-containing monofunctional (meth)acrylate and the polyfunctional (meth)acrylate are not compatible, and do not dissolve mutually at an arbitrary ratio. Therefore, sufficiently low refractive index cannot be achieved. On the contrary, the fluorine-containing bifunctional (meth)acrylate and the polyfunctional (meth)acrylate mutually dissolve at an arbitrary ratio. However, if the content of fluorine atoms in the cross-linked polymer is increased for reducing the refractive index, the cross-linking density is lowered. Accordingly, it is impossible to suffice both the low refractive index and the high surface hardness, and it is difficult to give sufficient surface hardness to the optical fibers and the reflection reducing films. Further, sufficient adhesion cannot be achieved.

There is also proposed fluorine-containing hydroxy (meth)acrylate for the purpose of improving the adhesion and for use as a starting material for other fluorine-containing (meth)acrylates (Japanese Laid-open Patent Application Nos. 4-321660, 4-356443, and 4-356444). However, since these compounds are monofunctional (meth)acrylate, the surface hardness after curing is low, and the abrasion resistance is inferior.

DISCLOSURE OF THE INVENTION

It is an object of the present invention to provide fluorine-containing polyfunctional (meth)acrylate which gives fluorine compounds having sufficiently low refractive index, sufficiently high surface hardness, and adhesion.

It is another object of the present invention to provide a low refractivity material having low refractive index and superior surface hardness, a reflection reducing film, and fluorine-containing monomer compositions which can be used as a starting material for such material and film.

According to the present invention, there is provided fluorine-containing polyfunctional (meth)acrylate represented by the formula (1):

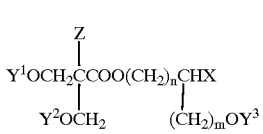

(1)

wherein X stands for a fluoroalkyl group having 1 to 14 carbon atoms and 3 or more fluorine atoms, or a fluorocycloalkyl group having 3 to 14 carbon atoms and 4 or more fluorine atoms; $Y^1$, $Y^2$, and $Y^3$ stand for a hydrogen atom, an acryloyl group or a methacryloyl group, and at least two of $Y^1$, $Y^2$, and $Y^3$ are the same or different groups and stand for an acryloyl group or a methacryloyl group; Z stands for a hydrogen atom or an alkyl group having 1 to 3 carbon atoms; and n and m stand for an integer of 0 or 1, and n+m=1.

According to the present invention, there is provided a fluorine-containing monomer composition comprising 5 to 100% by weight of said fluorine-containing polyfunctional (meth)acrylate represented by the formula (1) above.

According to the present invention, there is further provided a composition comprising the fluorine-containing polyfunctional (meth)acrylate represented by the formula (1) above and powders of an inorganic compound in total of 5 to 100% by weight of the composition.

According to the present invention, there is further provided a low refractivity material having refractive index of 1.49 or lower prepared by a method comprising the step of curing the fluorine-containing monomer composition or the composition containing the powders of an inorganic compound by polymerization.

According to the present invention, there is provided a reflection reducing film comprising a transparent substrate, a layer of the low refractivity material above, and optionally at least one material layer between the transparent substrate and the layer of the low refractivity material.

PREFERRED EMBODIMENTS OF THE PRESENT INVENTION

Figure 1:
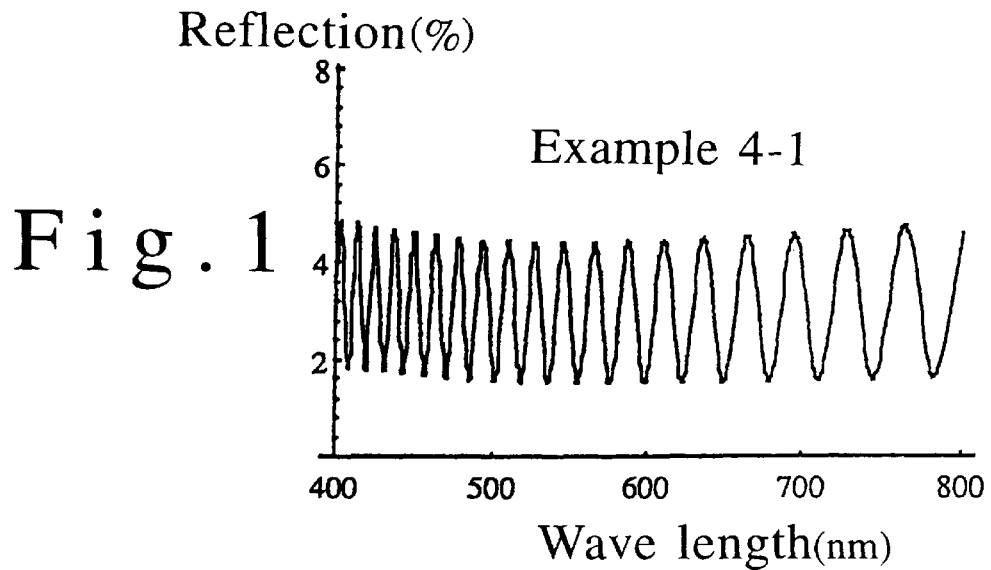
FIG. 1 is a graph showing the results of the measurements of the spectral reflectance in Example 4-1.

The fluorine-containing polyfunctional (meth)acrylate of the present invention is represented by the formula (1) above, wherein when n=1 and m=0, the fluorine-containing polyfunctional (meth)acrylate is represented by the formula (1a) below, and when n=0 and m=1, by the formula (1b) below.

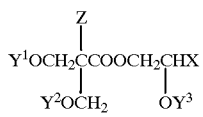 (1a)

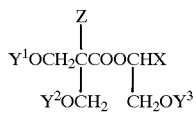 (1b)

Specifically, the present fluorine-containing polyfunctional (meth)acrylate may be a fluorine-containing bifunctional (meth)acrylate having (meth)acryloyl groups and a hydroxyl group and represented by the formula (1a) wherein two of $Y^1$, $Y^2$ and $Y^3$ stand for an acryloyl group or a methacryloyl group, and the remaining one of $Y^1$, $Y^2$ and $Y^3$ stands for a hydrogen atom (referred to hereinbelow as diester A); a fluorine-containing bifunctional (meth)acrylate having (meth)acryloyl groups and a hydroxyl group and represented by the formula (1b) wherein two of $Y^1$, $Y^2$ and $Y^3$ stand for an acryloyl group or a methacryloyl group, and the remaining one of $Y^1$, $Y^2$ and $Y^3$ stands for a hydrogen atom (referred to hereinbelow as diester B); a fluorine-containing trifunctional (meth)acrylate of the formula (1a) wherein $Y^1$, $Y^2$ and $Y^3$ are the same or different groups and stand for an acryloyl group or a methacryloyl group (referred to hereinbelow as triester A); or a fluorine-containing trifunctional (meth)acrylate of the formula (1b) wherein $Y^1$, $Y^2$ and $Y^3$ are the same or different groups and stand for an acryloyl group or a methacryloyl group (referred to hereinbelow as triester B). In the formula (1), if X has more than 12 carbon atoms, the manufacture of the fluorine-containing polyfunctional (meth)acrylate becomes difficult.

Preferred examples of diester A may include
3-perfluorohexyl-2-hydroxypropyl 2,2-bis((meth)acryloyloxymethyl)propionate,
3-perfluorohexyl-2-((meth)acryloyloxy)propyl 2-((meth)acryloyloxymethyl)-2-(hydroxymethyl)propionate,
3-perfluorooctyl-2-hydroxypropyl 2,2-bis((meth)acryloyloxymethyl)propionate, and
3-perfluorooctyl-2-((meth)acryloyloxy)propyl 2-((meth)acryloyloxymethyl)-2-(hydroxymethyl)propionate.

Preferred examples of diester B may include
2-perfluorohexyl-(1-hydroxymethyl)ethyl 2,2-bis((meth)acryloyloxymethyl)propionate,
2-perfluorohexyl-1-((meth)acryloyloxymethyl)ethyl 2-((meth)acryloyloxymethyl)-2-(hydroxymethyl)propionate,
2-perfluorooctyl-(1-hydroxymethyl)ethyl 2,2-bis((meth)acryloyloxymethyl)propionate, and
2-perfluorooctyl-1-((meth)acryloyloxymethyl)ethyl 2-((meth)acryloyloxymethyl)-2-(hydroxymethyl)propionate.

Preferred examples of triester A may include
3-perfluorobutyl-2-(meth)acryloyloxypropyl 2,2-bis((meth)acryloyloxymethyl)propionate,
3-perfluorohexyl-2-(meth)acryloyloxypropyl 2,2-bis((meth)acryloyloxymethyl)propionate,
3-perfluorooctyl-2-(meth)acryloyloxypropyl 2,2-bis((meth)acryloyloxymethyl)propionate,
3-perfluorocyclopentylmethyl-2-(meth)acryloyloxypropyl 2,2-bis((meth)acryloyloxymethyl)propionate,
3-perfluorocyclohexylmethyl-2-(meth)acryloyloxypropyl 2,2-bis((meth)acryloyloxymethyl)propionate, or 3-perfluorocycloheptylmethyl-2-(meth)acryloyloxypropyl 2,2-bis((meth)acryloyloxymethyl)propionate.

Preferred examples of triester B may include
2-perfluorobutyl-(1-(meth)acryloyloxymethyl)ethyl 2,2-bis((meth)acryloyloxymethyl)propionate,
2-perfluorohexyl-(1-(meth)acryloyloxymethyl)ethyl 2,2-bis((meth)acryloyloxymethyl)propionate,
2-perfluorooctyl-(1-(meth)acryloyloxymethyl)ethyl 2,2-bis((meth)acryloyloxymethyl)propionate,
2-perfluorocyclopentylmethyl-(1-(meth)acryloyloxymethyl)ethyl 2,2-bis((meth)acryloyloxymethyl)propionate,
2-perfluorocyclohexylmethyl-(1-(meth)acryloyloxymethyl)ethyl 2,2-bis((meth)acryloyloxymethyl)propionate, or
2-perfluorocycloheptylmethyl-(1-(meth)acryloyloxymethyl)ethyl 2,2-bis((meth)acryloyloxymethyl)propionate.

The above mentioned diester A, diester B, triester A, and triester B may be used alone or as a mixture as a starting material for a resin with low refractive index (a mixture of diester A and diester B is referred to as "diester mixture", a mixture of triester A and triester B is referred to as "triester mixture", and a mixture of diester and triester, or the diester mixture and the triester mixture are collectively referred to as "ester mixture" in some cases hereinbelow.

The following two methods may be enumerated as examples of preferable methods for producing the fluorine-containing polyfunctional (meth)acrylate of the present invention.

The first method includes the steps of (a) reacting carboxylic acid having two hydroxymethyl groups represented by the following formula (2) (referred to hereinbelow as "carboxylic acid C") and fluorine-containing diepoxide represented by the following formula (3) (referred to hereinbelow as "epoxide D") in the presence of a catalyst according to an ordinary ring-opening reaction to obtain a mixture of hydroxyfluoroalkyl 2,2-bis(hydroxymethyl)carboxylates represented by the following formulae (4) and (5) (both respectively referred to hereinbelow as "ester E"), and (b) esterifying the ester E's with (meth)acryloylchloride, to produce an ester mixture.

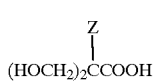

(2)

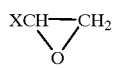

(3)

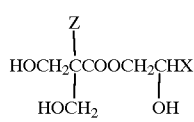

(4)

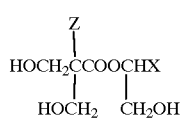

(5)

(in the formulae, X and Z are the same as X and Y in formula (1))

Preferable examples of carboxylic acid C for use in the reaction (a) may include
2,2-bis(hydroxymethyl)acetic acid,
2,2-bis(hydroxymethyl)propionic acid,
2,2-bis(hydroxymethyl)butyric acid, and
2,2-bis(hydroxymethyl)valeric acid. Preferable examples of epoxide D may include
3-trifluoromethyl-1,2-epoxypropane,
3-perfluoroethyl-1,2-epoxypropane,
3-perfluoropropyl-1,2-epoxypropane,
3-perfluorobutyl-1,2-epoxypropane,
3-perfluoropentyl-1,2-epoxypropane,
3-perfluorohexyl-1,2-epoxypropane,
3-perfluoroheptyl-1,2-epoxypropane,
3-perfluorooctyl-1,2-epoxypropane,
3-perfluorononyl-1,2-epoxypropane,
3-perfluorodecyl-1,2-epoxypropane,
3-perfluoroundecyl-1,2-epoxypropane,
3-perfluorododecyl-1,2-epoxypropane,
3-perfluorotridecyl-1,2-epoxypropane,
3-(perfluoro-1-methylethyl)-1,2-epoxypropane,
3-(perfluoro-2-methylpropyl)-1,2-epoxypropane,
3-(perfluoro-3-methylbutyl)-1,2-epoxypropane,
3-(perfluoro-4-methylpentyl)-1,2-epoxypropane,
3-(perfluoro-5-methylhexyl)-1,2-epoxypropane,
3-(perfluoro-6-methylheptyl)-1,2-epoxypropane,
3-(perfluoro-7-methyloctyl)-1,2-epoxypropane,
3-(perfluoro-8-methylnonyl)-1,2-epoxypropane,
3-(perfluoro-9-methyldecyl)-1,2-epoxypropane,
3-(perfluoro-10-methylundecyl)-1,2-epoxypropane,
3-(perfluoro-11-methyldodecyl)-1,2-epoxypropane, and
3-(perfluoro-12-methyltridecyl)-1,2-epoxypropane.

For reacting carboxylic acid C and epoxide D in reaction (a), it is preferred to charge 0.8 to 5 mol, more preferably 1.0 to 1.8 mol of carboxylic acid C per 1 mol of epoxide D.

Examples of the catalyst used in reaction (a) may include tertiary amines such as triethylamine or benzyldimethylamine; or quaternary ammonium salts such as tetraethylammonium bromide or tetramethylammonium bromide. The amount of the catalyst is preferably 0.001 to 5% by weight, more preferably 0.01 to 2.5% by weight of the total weight of the reaction mixture.

The temperature for the reaction (a) is preferably 40 to 200° C., more preferably 80 to 120° C. The duration of the reaction is preferably 1 to 48 hours, more preferably 2 to 12 hours.

The mixture of ester E's obtained by the reaction (a) may be, before it is subjected to step (b), dissolved in an organic solvent such as chloroform, methylene chloride, trifluoromethylbenzene, ethyl acetate or mixtures thereof, and washed with an alkaline aqueous solution such as sodium hydroxide or sodium carbonate, for removing the catalyst, depending on the need. The mixture of ester E's may be purified by vacuum distillation, recrystallization, or column chromatography.

For reacting ester E and (meth)acryloylchloride in reaction (b) to produce a diester mixture, it is preferred to charge 1.6 to 10 mol, more preferably 2.0 to 4.0 mol of (meth)acryloylchloride per 1 mol of ester E. On the other hand, to produce a triester mixture, it is preferred to charge 2.4 to 15 mol, more preferably 3.0 to 6.0 mol of (meth)acryloylchloride per 1 mol of ester E.

In reaction (b), base such as tertiary alkylamine, for example, triethylamine or benzyldimethylamine, or pyridine may be added to the reaction mixture for capturing hydrochloric acid generated during the reaction. The amount of base is preferably 1.6 to 10.0 mol, more preferably 2.0 to 4.5 mol per 1 mol of ester E, for producing a diester mixture. On the other hand, for producing triester mixture, the amount of base is preferably 2.4 to 15.0 mol, more preferably 3.0 to 7.0 per 1 mol of ester E.

It is preferred to proceed with reaction (b) in a suitable solvent. Examples of such a solvent may include chloroform, methylene chloride, trifluoromethylbenzene, or mixtures thereof. The amount of the solvent is preferably 20 to 2000 parts by weight, more preferably 100 to 500 parts by weight based on 100 parts by weight of the total amount of ester E, (meth)acryloylchloride, and the base.

The temperature for reaction (b) is preferably −60 to 20° C., more preferably −40 to 0° C., and the duration of reaction (b) is preferably 0.1 to 12 hours, more preferably 0.5 to 2 hours.

After the completion of reaction (b), the resulting system including the generated ester mixture may be subjected to a variety of treatments depending on the need. For example, a small amount of alcohols such as methanol or ethanol, or water may be added to the reaction system for decomposing the excess (meth)acryloylchloride in the reaction system. The reaction system may also be washed with an acid aqueous solution such as diluted hydrochloric acid. The reaction system may also be subjected to purification such as vacuum distillation, recrystallization or column chromatography. In the vacuum distillation, it is preferred to add a polymerization inhibitor such as hydroquinone, hydroquinone monoethyl ether, or tert-butylcatechol to the system for inhibiting polymerization. The amount of the polymerization inhibitor is preferably 0.001 to 2% by weight, more preferably 0.005 to 0.2% by weight of the total weight of the mixture resulting from the reaction (c).

The diester mixture generated by the reaction (b) is usually a mixture of four structural isomers composed of two sorts of diester A and two sorts of diester B. Specifically, the isomers are diester $A^1$ represented by the formula (6), diester $A^2$ represented by the formula (7), diester $B^1$ represented by the formula (8), and diester $B^2$ represented by the formula (9):

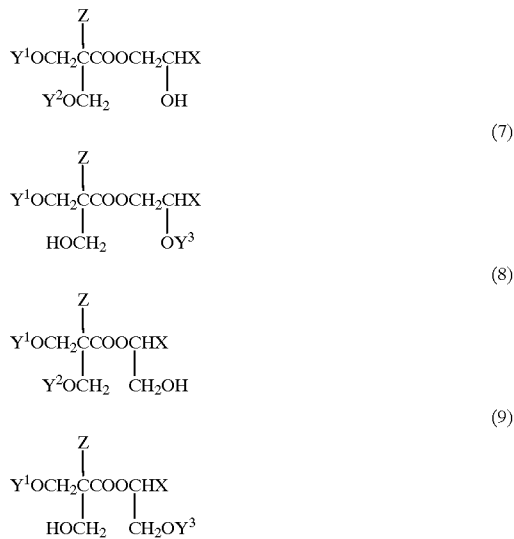

(in the formulae, X, $Y^1$, $Y^2$, $Y^3$ and Z are the same as X, $Y^1$, $Y^2$, $Y^3$ and Z in the formula (1))

The objective compound may be obtained by separation and isolation of diester $A^1$, diester $A^2$, diester $B^1$ or diester $B^2$, or diester A consisting of diester $A^1$ and diester $A^2$, or diester B consisting of diester $B^1$ and diester $B^2$. On the other hand, the resulting triester mixture is a mixture of structural isomers triester A and triester B. Thus, in the same manner as for diester A and diester B, the objective compound may be obtained by separating and isolating the triester A and triester B from the triester mixture. In either case, the separating and isolating methods may include, for example, liquid chromatography for separation.

The second method includes the steps of (c) producing 2,2-bis((meth)acryloyloxymethyl)carboxylic acid represented by the following formula (10) (referred to hereinbelow as carboxylic acid F) from the aforementioned carboxylic acid C by a method, for example, as described in Japanese Laid-open Patent Application No.63-99038, that is, by reacting the aforementioned carboxylic acid C with (meth)acrylic acid, (meth)acryloylchloride or (meth)acrylate in the presence of, if needed, any suitable catalyst

(10)

(in the formula, $Y^1$, $Y^2$ and Z are the same as $Y^1$, $Y^2$ and Z in the formula (1)), and (d) reacting the carboxylic acid F with the aforementioned epoxide D in the presence of a catalyst according to an ordinary ring-opening reaction, to obtain an ester mixture. The resulting ester mixture is a mixture of diester $A^1$ represented by the formula (6) and diester $B^1$ represented by the formula (8).

For reacting carboxylic acid C and (meth) acryloylchloride in reaction (c), it is preferred to charge 1.6 to 10 mol, more preferably 2.0 to 4.0 mol of (meth) acryloylchloride per 1 mol of carboxylic acid C.

In reaction (c), base such as tertiary alkylamine, for example, triethylamine or benzyldimethylamine, or pyridine may be added to the reaction system for capturing the hydrochloric acid generated during the reaction. The amount of base is preferably 1.6 to 10 mol, more preferably 2.0 to 4.5 mol per 1 mol of carboxylic acid C.

It is preferred to proceed with reaction (c) in a suitable solvent. Examples of such a solvent may include chloroform, methylene chloride, trifluoromethylbenzene, and the like. The amount of the solvent is preferably 20 to 2000 parts by weight, more preferably 100 to 500 parts by weight based on 100 parts by weight of the total amount of carboxylic acid C, (meth)acryloylchloride, and the base.

The temperature for reaction (c) is preferably −60 to 20° C., more preferably −40 to 0° C., and the duration of reaction (c) is preferably 0.1 to 12 hours, more preferably 0.5 to 2 hours.

Carboxylic acid F produced by the reaction (c) may be subjected to a variety of treatments depending on the need, before subsequent treatment (d). For example, a small amount of alcohols such as methanol or ethanol or water may be added to the reaction system for decomposing the excess (meth)acryloylchloride in the reaction system. Carboxylic acid F may also be washed with an acid aqueous solution such as diluted hydrochloric acid. Carboxylic acid F may also be purified by vacuum distillation, recrystallization or column chromatography. In the vacuum distillation, it is preferred to add a polymerization inhibitor such as hydroquinone, hydroquinone monoethyl ether, or tert-butylcatechol to the system for inhibiting polymerization. The amount of the polymerization inhibitor is preferably 0.001 to 2.0% by weight, more preferably 0.005 to 0.2% by weight of the total weight of the mixture after the reaction.

For reacting the epoxide D and carboxylic acid F in the reaction (d), the mixing ratio of carboxylic acid F is preferably 0.8 to 5 mol, more preferably 1.0 to 1.8 mol per 1 mol of epoxide D.

Examples of the catalyst used in reaction (d) may include publicly known catalysts such as tertiary amines including triethylamine or benzyldimethylamine; or quaternary ammonium salts including tetraethylammonium bromide or tetramethylammonium bromide. The amount of the catalyst is preferably 0.001 to 5.0% by weight, more preferably 0.01 to 2.5% by weight of the total weight of the reaction mixture.

In the reaction (d), it is preferred to add a polymerization inhibitor to the reaction system. Preferable polymerization inhibitors may include hydroquinone, hydroquinone monoethyl ether, or tert-butylcatechol. The amount of the polymerization inhibitor is preferably 0.001 to 2% by weight, more preferably 0.005 to 0.2% by weight of the total weight of the reaction mixture.

The temperature for the reaction (d) is preferably 40 to 200° C., more preferably 80 to 120° C. The duration of the reaction (d) is preferably 1 to 48 hours, more preferably 2 to 12 hours.

After the completion of reaction (d), the resulting mixture containing the generated diester mixture may be subjected to a variety of treatments depending on the need before use. For example, the mixture may be dissolved in an organic solvent such as chloroform, methylene chloride or trifluoromethylbenzene, and then washed with an alkaline aqueous solution such as sodium hydroxide or sodium carbonate, for removing the catalyst. The mixture may be purified by vacuum distillation, recrystallization, column chromatography, and the like, depending on the need. In the vacuum distillation, it is preferred to add a polymerization inhibitor such as hydroquinone, hydroquinone monoethyl ether, or tert-butylcatechol to the mixture for inhibiting polymerization. The amount of the polymerization inhibitor is preferably 0.001 to 2% by weight, more preferably 0.005 to 0.2% by weight of the total weight of the mixture resulting from the reaction.

On the other hand, a triester mixture may be produced by (e) esterifying the diester mixture obtained by the reactions (c) and (d) with one equivalent of additional (meth)acryloylchloride.

For reacting the diester mixture and (meth)acryloylchloride in reaction (e), it is preferred to charge 0.8 to 5 mol, more preferably 1.0 to 2.0 mol of (meth)acryloylchloride per 1 mol of the diester mixture.

In reaction (e), base such as tertiary alkylamine, for example, triethylamine or benzyldimethylamine, or pyridine may be added to the reaction system for capturing hydrochloric acid generated during the reaction. The amount of base is preferably 0.8 to 5.0 mol, more preferably 1.0 to 2.5 mol per 1 mol of the diester mixture.

It is preferred to proceed with reaction (e) in a suitable solvent. Examples of such a solvent may include chloroform, methylene chloride, trifluoromethylbenzene, and the like. The amount of the solvent is preferably 20 to 2000 parts by weight, more preferably 100 to 500 parts by weight based on 100 parts by weight of the total amount of the diester mixture, (meth)acryloylchloride, and the base.

The temperature for reaction (e) is preferably −60 to 20° C., more preferably −40 to 0° C., and the duration of reaction (e) is preferably 0.1 to 12 hours, more preferably 0.5 to 2 hours.

After the completion of reaction (e), the resulting system containing generated ester mixture may be subjected to a variety of treatments depending on the need. For example, a small amount of alcohols such as methanol or ethanol, or water may be added to the reaction system for decomposing the excess (meth)acryloylchloride in the reaction system. The reaction system may also be washed with an acid aqueous solution such as diluted hydrochloric acid. The reaction system may also be subjected to purification such as vacuum distillation, recrystallization or column chromatography. In the vacuum distillation, it is preferred to add a polymerization inhibitor such as hydroquinone, hydroquinone monoethyl ether, or tert-butylcatechol to the system for inhibiting polymerization. The amount of the polymerization inhibitor is preferably 0.001 to 2% by weight, more preferably 0.005 to 0.2% by weight of the total weight of the mixture resulting from the reaction (e).

The triester mixture generated by the reaction (e) is a mixture of structural isomers triester A and triester B. The objective compound may be obtained by separation and isolation of triester A and triester B. The separation and isolation may be performed, for example, by liquid chromatography for separation.

The fluorine-containing polyfunctional (meth)acrylate itself of the present invention may be cured by cross-linking to produce a cured film having excellent abrasion resistance and adhesion, and may be used alone or as a mixture.

The composition of the present invention contains the fluorine-containing polyfunctional(meth)acrylate, or both the fluorine-containing polyfunctional (meth)acrylate and powders of an inorganic compound. The fluorine-containing polyfunctional (meth)acrylate is a compound represented by the formula (1), and may specifically be a fluorine-containing polyfunctional (meth)acrylate selected from the group consisting of the aforementioned diester $A^1$, diester $A^2$, diester $B^1$, diester $B^2$, triester A, triester B and mixtures thereof (sometimes collectively referred to as polyfunctional ester A hereinbelow). As the mixture, various ester mixtures obtained during the aforementioned method of producing the polyfunctional ester A may be directly used.

The content of polyfunctional ester A is 5 to 100% by weight, preferably 10 to 100% by weight of the total weight of the composition. On the other hand, the content of the powders of the inorganic compound is preferably less than 90% by weight of the total weight of the composition. When the composition is cured by polymerization, it is cross-linked to acquire three-dimensional net work structure, thereby giving a cured film having excellent abrasion resistance, adhesion, wear resistance, heat resistance, and weatherability.

There is no particular limitation to the powders of the inorganic compound, but it is preferably a compound having the refractive index of 1.5 or lower. Specifically, powders of magnesium fluoride (refractive index 1.38), silicon oxide (refractive index 1.46), aluminum fluoride (refractive index 1.33 to 1.39), calcium fluoride (refractive index 1.44), lithium fluoride (refractive index 1.36 to 1.37), sodium fluoride (refractive index 1.32 to 1.34), or thorium fluoride (refractive index 1.45 to 1.50) are preferable. The particle size of the powders is preferably sufficiently smaller than the wave length of the visible radiation for the purpose of ensuring the transparency of the low refractivity material. Specifically, the particle size is preferably not larger than 100 nm, more preferably not larger than 50 nm.

The inorganic powders is used preferably in the form of an organic sol in which the powders are previously dispersed in an organic dispersion medium, for preventing the decreasing of dispersion stability in the composition and of adhesion in the low refractivity material. Further, for increasing the dispersion stability in the composition and adhesion in the low refractivity material, the surface of the inorganic powder composition may be modified with various coupling agents. The various coupling agents may include, for example, silicide substituted by organic residues; alkoxides of metals such as aluminum, titanium, zirconium, antimony, or mixtures thereof; salts of organic acids; and coordination compounds combined with compounds which can be coordinated.

The composition of the present invention may optionally contain preferably less than 95% by weight, more preferably less than 90% by weight other curing materials such as ordinary thermosetting monomers or energy-beam curable monomers. Preferred examples of the thermosetting monomers and energy-beam curable monomers may include polyfunctional monomers having two or more polymerizable unsaturated groups, for example, polyalkylene glycol di(meth)acrylate such as dipentaerythritol hexa(meth) acrylate, dipentaerythritol penta(meth)acrylate, dipentaerythritol tetra(meth)acrylate, pentaerythritol tetra(meth) acrylate, pentaerythritol tri(meth)acrylate, pentaerythritol di(meth)acrylate, ditrimethylolpropane tetra(meth)acrylate, ditrimethylolpropane tri(meth)acrylate, ditrimethylolpropane di(meth)acrylate, trimethylolpropane tri(meth)acrylate, trimethylolpropane di(meth)acrylate, tetramethylolmethane tetraacrylate, 1,1,1-tris(acryloyloxyethoxyethoxy)propane, 2,2-bis(4-acryloyloxyethoxyethoxyphenyl)propane, 2,2-bis (4-acryloyloxyethoxyethoxycyclohexyl)propane, 2,2-bis(4-acryloyloxyethoxyethoxyphenyl)methane, neopentyl glycol di(meth)acrylate, hydrogenated dicyclopentadienyl di(meth) acrylate, tris(hydroxyethyl)isocyanurate triacrylate, tris (hydroxyethyl)isocyanurate diacrylate, 1,4-butanediol di(meth)acrylate, 1,6-hexanediol di(meth)acrylate, isobornyl di(meth)acrylate, polyethylene glycol di(meth) acrylate, polypropylene glycol di(meth)acrylate, or polytetramethylene glycol di(meth)acrylate. These may be used alone or as a mixture.

The composition of the present invention may optionally contain monofunctional (meth)acrylate as long as the desired effect of the present invention is not deteriorated. Such monofunctional (meth)acrylate may preferably be fluorine-containing monofunctional (meth)acrylate in view of the purpose of lowering the refractive index of the monomer composition, such as 2,2,2-trifluoroethyl(meth) acrylate, 2,2,3,3,3-pentafluoropropyl(meth)acrylate, 2,2,3,3, 4,4,4-heptafluorobutyl(meth)acrylate, 2,2,3,3,4,4,5,5,5-nonafluoropentyl(meth)acrylate, 2,2,3,3,4,4,5,5,6,6,6-undecafluorohexyl(meth)acrylate, 2,2,3,3,4,4,5,5,6,6,7,7,7-tridecafluoroheptyl(meth)acrylate, 2,2,3,3,4,4,5,5,6,6,7,7,8, 8,8-pentadecafluorooctyl(meth)acrylate, 3,3,4,4,5,5,6,6,7,7, 8,8,8-tridecafluorooctyl(meth)acrylate, 2,2,3,3,4,4,5,5,6,6,7, 7,8,8,9,9,10,10,10-nonadecafluorodecyl(meth)acrylate, 3,3, 4,4,5,5,6,6,7,7,8,8,9,9,10,10,10-heptadecafluorodecyl (meth)acrylate, 2-trifluoromethyl-3,3,3-trifluoropropyl (meth)acrylate, 3-trifluoromethyl-4,4,4-trifluorobutyl(meth) acrylate, 1-methyl-2,2,3,3,3-pentafluoropropyl(meth) acrylate, or 1-methyl-2,2,3,3,4,4,4-heptafluorobutyl(meth) acrylate. These may be used alone or as a mixture.

The composition of the present invention may also contain, if necessary, fluorine-containing bifunctional (meth)acrylate other than the diester mixture as a curing material as long as the desired effect of the present invention is not deteriorated. Preferred examples of the fluorine-containing bifunctional (meth)acrylate other than the diester mixtures may include 2,2,2-trifluoroethylethylene glycol di(meth)acrylate, 2,2,3,3,3-pentafluoropropylethylene glycol di(meth)acrylate, 2,2,3,3,4,4,4-heptafluorobutylethylene glycol di(meth)acrylate, 2,2,3,3,4,4,5,5,5-nonafluoropentylethylene glycol di(meth)acrylate, 2,2,3,3,4, 4,5,5,6,6,6-undecafluorohexylethylene glycol di(meth) acrylate, 2,2,3,3,4,4,5,5,6,6,7,7,7-tridecafluoroheptylethylene glycol di(meth)acrylate, 2,2,3,3, 4,4,5,5,6,6,7,7,8,8,8-pentadecafluorooctylethylene glycol di(meth)acrylate, 2,2,3,3,4,4,5,5,6,6,7,7,8,8,9,9,10,10,10-nonadecafluorodecylethylene glycol di(meth)acrylate, 2,2,3, 3-tetrafluorobutanediol di(meth)acrylate, 2,2,3,3,4,4-hexafluoropentadiol di(meth)acrylate, 2,2,3,3,4,4,5,5-octafluorohexanediol di(meth)acrylate, 2,2,3,3,4,4,5,5,6,6-decafluoroheptanediol di(meth)acrylate, 2,2,3,3,4,4,5,5,6,6, 7,7-dodecafluorooctanediol di(meth)acrylate, 2,2,3,3,4,4,5, 5,6,6,7,7,8,8-tetradecafluorononanediol di(meth)acrylate, 2,2,3,3,4,4,5,5,6,6,7,7,8,8,9,9-hexadecafluorodecanediol di(meth)acrylate, 2,2,3,3,4,4,5,5,6,6,7,7,8,8,9,9,10,10-octadecafluoroundecanediol di(meth)acrylate, or 2,2,3,3,4, 4,5,5,6,6,7,7,8,8,9,9,10,10,11,11-eicosafluorododecanediol di(meth)acrylate. These may be used alone or as a mixture.

The composition of the present invention may optionally be mixed with a polymer for improving the film forming property. The polymer to be added is not particularly limited, but preferably a polymer of fluorine-containing (meth) acrylate, or a copolymer of fluorine-containing (meth) acrylate with other monomers. The mixing ratio of the polymer is preferably 25 parts by weight or less, more preferably 10 parts by weight or less based on 100 parts by weight of the curing materials in the monomer composition.

The low refractivity material of the present invention is prepared by curing the above-mentioned composition by polymerization, and has the refractive index of 1.49 or lower, more preferably 1.35 to 1.49.

The curing by polymerization may be carried out by optionally admixing a curing initiator and/or a solvent such as isopropylalcohol or toluene to the monomer composition; applying the resulting mixture to a substrate such as a transparent substrate by an ordinary coating method such as roll coating method, gravure coating method, dip coating method, or spin coating method; drying; and curing by heating or irradiation with active energy beam such as ultraviolet ray, electron beam, or radio active ray. The conditions for curing by polymerization may suitably be selected depending on the curing materials in the composition. When the low refractivity material is formed into a film, the film thickness may suitably be selected depending on the purpose.

Examples of the curing initiator may include azo radical polymerization initiators such as azobisisobutyronitrile, azobiscyclohexanecarbonitrile, or azobisvaleronitrile; radical polymerization initiators of organic peroxide type such as benzoyl peroxide, tert-butylhydroperoxide, cumene peroxide, or diacylperoxide; or photopolymerization initiators such as benzoin compounds including benzoin, benzoin methyl ether, benzoin ethyl ether, or benzoin isopropyl ether, carbonyl compounds including benzyl, benzophenone, acetophenone, or Michler's ketone, azo compounds including azobisisobutyronitrile or azodibenzoyl, or a mixture of α-diketone and a tertiary amine. The amount of the curing initiator may be 0.01 to 10% by weight of the total weight of the curing materials in the monomer composition and the curing initiator.

The reflection reducing film of the present invention has a transparent substrate and a layer of the low refractivity material. The layer of the low refractivity material preferably has a suitable thickness. The suitable thickness is preferably selected so that the wave length which indicated the minimum reflectance of the reflection reducing film is usually 420 to 720 nm, more preferably 520 to 620 nm.

The kind of the transparent substrate is not particularly limited as long as the substrate is transparent. Usually, a PET (polyethylene terephthalate) film, a TAC (triacetyl cellulose) film, an acryl film, or a polycarbonate film may be used.

The reflection reducing film of the present invention may be composed of the transparent substrate and the layer of the low refractivity material thereon, or of the transparent substrate, the layer of the low refractivity material, and at least one material layer therebetween. The material layer may be a layer of a high refractivity material for improving the reflection reducing effect. The layer of the high refractivity material preferably has the refractive index of 1.55 or higher, and the thickness of the layer may preferably be selected so that the wave length which indicated the maximum reflectance of the film provided with the layer of the high refractivity material is usually 400 to 900 nm.

The transparent substrate may be provided with one layer of the low refractivity material and one layer of the high refractivity material, or it may be provided with two or more layers of each material. When two or more layers of each material are provided, the layers of the low refractivity material and the high refractivity material may be laminated alternately, with the outermost layer being of the low refractivity material. When two or more layers of each material are provided, each layer of the low refractivity material or the high refractivity material may be made of the same or different materials.

The layer of the low refractivity material may be formed by optionally admixing a curing initiator and/or a solvent such as isopropylalcohol or toluene to the fluorine-containing composition; applying the resulting mixture to a substrate such as a transparent substrate by an ordinary coating method such as roll coating method, gravure coating method, dip coating method, or spin coating method; drying; and curing by heating or irradiation with active energy beam such as ultraviolet ray, electron beam, or radio active ray. The conditions for curing by polymerization may suitably be selected depending on the curing materials in the composition. The layer of the high refractivity material may be formed in the same way.

The reflection reducing film of the present invention may be provided with a hard coating for further improving the abrasion resistance of the reflection reducing film. The hard coating may be provided between the laminated layers of the low refractivity material and the high refractivity material and the transparent substrate. The kind of the hard coating is not particularly limited, and may be made of an ordinary resin for hard coating prepared from the polyfunctional monomer having two or more polymerizable unsaturated groups. However, if the difference in the refractive index of the transparent substrate and the hard coating is too large, reflection will occur at the interface therebetween. Thus, the difference in the refractive index of the transparent substrate and the hard coating is preferably kept as small as possible. The thickness of the hard coating is preferably 1 to 10 μm, more preferably 3 to 5 μm. The method of forming the hard coating is not particularly limited, and may include applying the hard coating material to a substrate such as a transparent substrate by an ordinary coating method such as roll coating method, gravure coating method, dip coating method, or spin coating method; drying; and curing by an ordinary method using energy beam or heat.

Since the fluorine-containing polyfunctional (meth) acrylate of the preset invention has a plurality of (meth) acryloyl groups, it is cured by cross-linking polymerization to acquire three-dimensional net work structure, and gives a cured film having high surface hardness and excellent abrasion resistance, wear resistance, heat resistance, and weatherability. Further, the diester mixture having a hydroxyl group can improve the adhesion of the cured coating film. The obtained cured product has superior light transmittance and low refractive index as well as excellent adhesion, so that it is useful as a resin with low refractive index for antireflection films or clad materials for optical fibers which are required to have superior abrasion resistance and adhesion.

Since the composition of the present invention contains the particular fluorine-containing polyfunctional (meth) acrylate, the cured product prepared by polymerizing the composition has the properties of both the low refractive index and the hardness of (meth)acrylate, and the composition can be formed into a film by applying on a substrate and cured by polymerization, thereby preparing the low refractivity material of the present invention. The low refractivity material of the present invention has the properties of both the low refractive index and the hardness of (meth) acrylate, and has low refractive index and high surface hardness. Further, by using the diester mixture having a hydroxyl group, its adhesion to other materials is further improved. The composition of the present invention may further contain powders of an inorganic compound, in addition to the particular fluorine-containing polyfunctional (meth)acrylate. By admixing the inorganic compound, abrasion resistance of the obtained low refractivity material may further be increased.

The reflection reducing film of the present invention is provided with a layer of the low refractivity material, it has low refractive index, high surface hardness, and high adhesion, and may be applied to a variety of usage. Accordingly, by using the composition of the present invention, reflection reducing films having a layer of the low refractivity material with larger area may be produced continuously and effectively at a low cost, compared to the conventional vapor deposition of magnesium fluoride.

EXAMPLES

The present invention will now be explained with reference to Examples and Comparative Examples, but the present invention is not limited thereto.

Example 1-1

Into a reactor equipped with a stirrer, a cooling tube and a gas introducing tube, 476 g (1.0 mol) of 3-perfluorooctyl-1,2-epoxypropane, 161 g (1.5 mol) of 2-bis(hydroxymethyl) propionic acid, 6.4 g of tetraethylammonium bromide, and 600 ml of isopropylalcohol were charged, gradually heated up to 95 to 100° C. in an oil bath, stirred at this temperature for 4 hours, and then cooled down to the room temperature. To the resulting reaction liquid was added 5 liters of water for precipitating a paste. The precipitate is separated by filtration and then dissolved in 1000 ml of ethyl acetate, and the solution thus obtained was washed three times with 1000 ml of water. The solvent was removed from the washed solution under reduced pressure to obtain white crystals. The crystals are believed to be a mixture of compounds having structures represented by the following formulae (11) and (12).

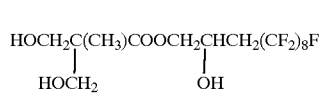
(11)

-continued

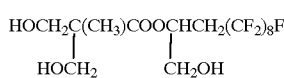
(12)

Into a reactor equipped with a stirrer, a thermometer, a gas introducing tube and a dropping funnel, the white crystals obtained by the above reaction, 303.6 g of triethylamine, and 1000 ml of chloroform were charged. Under ice cooling, 271.5 g (3.0 mol) of acryloylchloride were dissolved in 300 ml of chloroform, and the resulting solution was added dropwise to the reaction liquid from the dropping funnel while the temperature of the reaction liquid was kept below 5° C. After the completion of dropping, the reaction liquid was kept under ice cooling and stirred for two hours. Chloroform was then removed from the reaction liquid under reduced pressure, and the resulting yellow crystals were further purified by column chromatography using an ethyl acetate/n-hexane mixed solvent (1:4 by volume) as a developing solvent followed by removal of the solvent under reduced pressure, thereby obtaining 215 g of white crystal product G (yield 30%).

A portion of product G was further separated by high speed liquid chromatography. Separation was performed employing TSK gel Silica-60 (internal diameter of 21.5 mm: length of 300 mm: manufactured by TOSOH CORP.) as a column, and a mixed solvent of ethyl acetate/n-hexane (volume ratio 1:5), at flow rate of 5 ml per minute. For detection, an ultraviolet detector was employed at the wave length of 230 nm. As the result of analysis, the obtained compounds G-1, G-2, G-3 and G-4 were the compounds having the structures represented by the following formulae (13), (14), (15) and (16), respectively. The results of $^1$H-NMR, $^{19}$F-NMR, and Exact MS of these compounds thus obtained are shown below together with the structural formulae thereof.

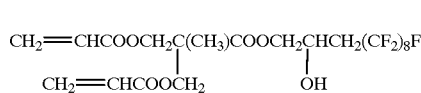
(13)

(Analytical results of G-1).

$^1$H-NMR($\delta$ (ppm)CDCl$_3$/TMS): 6.43(dd,2H); 6.11(dd, 1H); 6.11(dd,1H); 5.88(dd,2H); 4.53–4.31(m,1H); 4.43,4.36 (ABq,2H); 4.41,4.39(ABq,2H); 4.28,4.12(dABq,2H); 2.49–2.20(m,2H); 1.33(s,3H).

$^{19}$F-NMR($\delta$ (ppm)CDCl$_3$/CFCl$_3$):–123.10;–120.47;–119.72;–118.91; –118.60; –109.76; –77.79.

Exact MS: Measured value; 718.0865, Theoretical value;C$_{22}$H$_{19}$F$_{17}$O$_7$:718.0859.

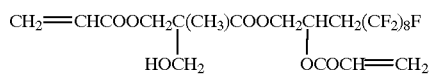
(14)

(Analytical results of G-2).

$^1$H-NMR($\delta$ (ppm)CDCl$_3$/TMS): 6.44(dd,1H); 6.42(dd, 1H); 6.12(dd,1H); 6.11(dd,1H); 5.89(dd,1H); 5.88(dd,1H); 5.38–5.35(m,1H); 4.43,4.34(ABq,2H); 4.28,4.12(dABq, 2H); 3.90,3.74(ABq,2H); 2.49–2.21(m,2H); 1.33(s,3H).

$^{19}$F-NMR($\delta$ (ppm)CDCl$_3$/CFCl$_3$):–123.11;–120.47;–119.72;–118.92; –118.60; –109.76; –77.79.

Exact MS: Measured value; 718.0862, Theoretical value; C$_{22}$H$_{19}$F$_{17}$O$_7$: 718.0859.

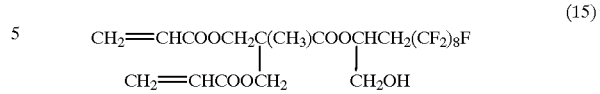
(15)

(Analytical results of G-3).

$^1$H-NMR($\delta$ (ppm)CDCl$_3$/TMS): 6.42(dd,2H); 6.11(dd, 1H); 6.11(dd,1H); 5.88(dd,2H); 5.38–5.34(m,1H); 4.43,4.36 (ABq,2H); 4.41,4.39(ABq,2H); 3.89,3.75(dABq,2H); 2.49–2.20(m,2H); 1.32(s,3H).

$^{19}$F-NMR ($\delta$ (ppm)CDCl$_3$/CFCl$_3$):–123.10;–120.47;–119.71;–118.91; –118.60; –109.76; –77.78.

Exact MS: Measured value; 718.0862, Theoretical value; C$_{22}$H$_{19}$F$_{17}$O$_7$:718.0859.

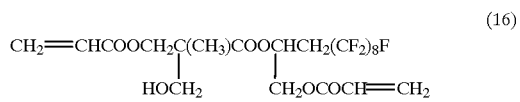
(16)

(Analytical results of G-4).

$^1$H-NMR($\delta$ (ppm)CDCl$_3$/TMS): 6.44(dd,1H); 6.42(dd, 1H); 6.12(dd,1H); 6.11(dd,1H); 5.89(dd,1H); 5.88(dd,1H); 5.39–5.34(m,1H); 4.43,4.36(ABq,2H); 4.29,4.13(dABq, 2H); 3.90,3.75(ABq,2H); 2.49–2.20(m,2H); 1.33(s,3H).

$^{19}$F-NMR ($\delta$ (ppm)CDCl$_3$/CFCl$_3$):–123.10;–120.46;–119.72;–118.91; –118.61; –109.76; –77.79.

Exact MS: Measured value; 718.0856, Theoretical value; C$_{22}$H$_{19}$F$_{17}$O$_7$: 718.0859.

Example 1-2

198 g of white crystal product H (yield 32%) was obtained in the same way as in Example 1-1 via the compounds of the structures represented by the formulae (17) and (18), except that 376.1 g (1.0 mol) of 3-perfluorohexyl-1,2-epoxypropane was employed instead of 3-perfluorooctyl-1, 2-epoxypropane.

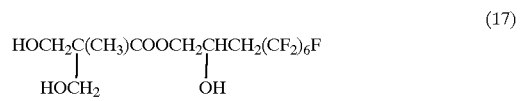
(17)

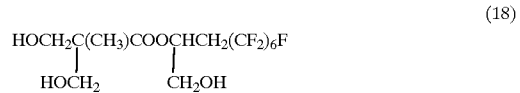
(18)

A portion of product H was separated by high speed liquid chromatography in the same way as in Example 1-1. The obtained compounds H-1, H-2, H-3 and H-4 were the compounds having the structures represented by the following formulae (19), (20), (21) and (22), respectively. The results of $^1$H-NMR, $^{19}$F-NMR, and Exact MS of these compounds thus obtained are shown below together with the structural formulae thereof.

$$CH_2=CHCOOCH_2\underset{\underset{CH_2=CHCOOCH_2}{|}}{C}(CH_3)COOCH_2\underset{\underset{OH}{|}}{C}HCH_2(CF_2)_6F \quad (19)$$

(Analytical results of H-1).

$^1$H-NMR($\delta$ (ppm)CDCl$_3$/TMS): 6.43(dd,2H); 6.12(dd,1H); 6.11(dd,1H); 5.88(dd,2H); 4.53–4.31(m,1H); 4.43,4.37 (ABq,2H); 4.41,4.39(ABq,2H); 4.28,4.12(dABq,2H); 2.49–2.21(m,2H); 1.34(s,3H).

$^{19}$F-NMR($\delta$ (ppm)CDCl$_3$/CFCl$_3$):−123.09;−120.39;−119.89;−118.89; −109.39; −77.90.

Exact MS: Measured value; 618.0931, Theoretical value; C$_{20}$H$_{19}$F$_{13}$O$_7$: 618.0923.

$$CH_2=CHCOOCH_2\underset{\underset{HOCH_2}{|}}{C}(CH_3)COOCH_2\underset{\underset{OCOCH=CH_2}{|}}{C}HCH_2(CF_2)_6F \quad (20)$$

(Analytical results of H-2).

$^1$H-NMR($\delta$ (ppm)CDCl$_3$/TMS): 6.44(dd,1H); 6.42(dd,1H); 6.11(dd,1H); 6.10(dd,1H); 5.88(dd,1H); 5.88(dd,1H); 5.38–5.35(m,1H); 4.43,4.34(ABq,2H); 4.28,4.12(dABq,2H); 3.90,3.75(ABq,2H); 2.49–2.21(m,2H); 1.32(s,3H).

$^{19}$F-NMR($\delta$ (ppm)CDCl$_3$/CFCl$_3$):−123.09;−120.39;−119.88;−118.89; −109.38; −77.90.

Exact MS: Measured value; 618.0921, Theoretical value; C$_{20}$H$_{19}$F$_{13}$O$_7$: 618.0923.

$$CH_2=CHCOOCH_2\underset{\underset{CH_2=CHCOOCH_2}{|}}{C}(CH_3)COOCHCH_2(CF_2)_6F\underset{\underset{CH_2OH}{|}}{} \quad (21)$$

(Analytical results of H-3).

$^1$H-NMR($\delta$ (ppm)CDCl$_3$/TMS): 6.42(dd,2H); 6.11(dd,1H); 6.11(dd,1H); 5.87(dd,2H); 5.37–5.34(m,1H); 4.43,4.36 (ABq,2H); 4.41,4.40(ABq,2H); 3.89,3.75(dABq,2H); 2.49–2.20(m,2H); 1.33(s,3H).

$^{19}$F-NMR($\delta$ (ppm)CDCl$_3$/CFCl$_3$):−123.08;−120.39;−119.88;−118.89; −109.39; −77.90.

Exact MS: Measured value; 618.0919, Theoretical value; C$_{20}$H$_{19}$F$_{13}$O$_7$: 618.0923.

$$CH_2=CHCOOCH_2\underset{\underset{HOCH_2}{|}}{C}(CH_3)COOCHCH_2(CF_2)_6F\underset{\underset{CH_2OCOCH=CH_2}{|}}{} \quad (22)$$

(Analytical results of H-4).

$^1$H-NMR($\delta$ (ppm)CDCl$_3$/TMS): 6.44(dd,1H); 6.42(dd,1H); 6.12(dd,1H); 6.11(dd,1H); 5.89(dd,1H); 5.87(dd,1H); 5.38–5.33(m,1H); 4.43,4.36(ABq,2H); 4.30,4.14(dABq,2H); 3.90,3.75(ABq,2H); 2.49–2.21(m,2H); 1.33(s,3H).

$^{19}$F-NMR($\delta$ (ppm)CDCl$_3$/CFCl$_3$):−123.09;−120.39;−119.88;−118.88; −109.39; −77.89.

Exact MS: Measured value; 618.0929, Theoretical value; C$_{20}$H$_{19}$F$_{13}$O$_7$: 618.0923.

Example 1-3

Into a reactor equipped with a stirrer, a thermometer a gas introducing tube and a dropping funnel, 201 g (1.5 mol) of 2,2-bis(hydroxymethyl)propionic acid, 304 g (3.0 mol) of trimethylamine and 600 ml of chloroform were charged. Under ice cooling, 406 g (4.5 mol) of acryloylchloride were dissolved in 400 ml of chloroform, and the resulting solution was added dropwise to the reaction liquid from the dropping funnel while the temperature of the reaction liquid was kept below 5° C. After the completion of dropping, the reaction liquid was kept under ice cooling and stirred for two hours. Chloroform was then removed from the reaction liquid under reduced pressure. Resulting yellow crystals were purified by column chromatography using as a developing solvent ethyl acetate/n-hexane mixed solvent (1:4 by volume). The solvent was then removed under reduced pressure to obtain 2,2-bis(acryloyloxymethyl)propionic acid as white crystals.

$$CH_2=CHCOOCH_2\underset{\underset{CH_2=CHCOOCH_2}{|}}{C}(CH_3)COOH \quad (23)$$

Into a reactor equipped with a stirrer, a cooling tube and a gas introducing tube, 290 g (1.2 mol) of 2,2-bis (acryloyloxymethyl)propionic acid obtained by the above reaction, 476 g (1.0 mol) of 3-perfluorooctyl-1,2-epoxypropane, 161 g (1.2 mol) of 2-bis(hydroxymethyl) propionic acid, 6.4 g of tetraethylammonium bromide, and 600 ml of isopropylalcohol were charged, and gradually heated up to 95 to 100° C. in an oil bath, stirred at this temperature for 4 hours, and then cooled down to the room temperature. To the resulting reaction liquid was added 5 liters of water for precipitating a paste. The precipitate was separated by filtration and then dissolved in 1000 ml of ethyl acetate, and the solution thus obtained was washed three times with 1000 ml of water. The solvent was removed from the washed solution under reduced pressure to obtain white crystal product I.

A portion of product I was further separated by high speed liquid chromatography in the same way as in Example 1-1. The obtained compounds I-1 and I-2 were the compounds having the structures represented by the above formulae (13) and (15), respectively. The results of $^1$H-NMR, $^{19}$F-NMR, and Exact MS of the obtained compounds are shown below.

(Analytical results of I-1).

$^1$H-NMR($\delta$ (ppm)CDCl$_3$/TMS): 6.44(dd,2H); 6.11(dd,1H); 6.11(dd,1H); 5.88(dd,2H); 4.54–4.31(m,1H); 4.43,4.36 (ABq,2H); 4.41,4.39(ABq,2H); 4.28,4.12(dABq,2H); 2.49–2.20(m,2H); 1.34(s,3H).

$^{19}$F-NMR($\delta$ (ppm)CDCl$_3$/CFCl$_3$):−123.10;−120.46;−119.72;−118.91; −118.60; −109.76; −77.78.

Exact MS: Measured value; 718.0856, Theoretical value; C$_{22}$H$_{19}$F$_{17}$O$_7$:718.0859.

(Analytical results of I-2).

$^1$H-NMR($\delta$ (ppm)CDCl$_3$/TMS): 6.42(dd,2H); 6.11(dd,1H); 6.11(dd,1H); 5.88(dd,2H); 5.37–5.34(m,1H); 4.43,4.36 (ABq,2H); 4.41,4.38(ABq,2H); 3.89,3.75(dABq,2H); 2.48–2.20(m,2H); 1.32(s,3H).

$^{19}$F-NMR($\delta$ (ppm)CDCl$_3$/CFCl$_3$):−123.10;−120.47;−119.72;−118.91; −118.60; −109.76; −77.79.

Exact MS: Measured value; 718.0852, Theoretical value; C$_{22}$H$_{19}$F$_{17}$O$_7$: 718.0859.

Example 2-1

Into a reactor equipped with a stirrer, a cooling tube, and a gas introducing tube, 476 g (1.0 mol) of 3-perfluorooctyl- 1,2-epoxypropane, 161 g (1.2 mol) of 2,2-bis(hydroxymethyl)propionic acid, 6.4 g of tetraethylammonium bromide and 600 ml of isopropylalcohol were charged, gradually heated up to 95 to 100° C. in an oil bath, stirred at this temperature for 4 hours, and then cooled down to the room temperature. To the resulting reaction liquid was added 5 liters of water for precipitating a paste. The precipitate was separated by filtration and then dissolved in 1000 ml of ethyl acetate, and the solution thus obtained was washed three times with 1000 ml of water. The solvent was removed from the washed solution under reduced pressure to obtain white crystals. These white crystals are believed to be a mixture of compounds having structures represented by the above formulae (11) and (12).

Into a reactor equipped with a stirrer, a thermometer, a gas introducing tube and a dropping funnel, 535 g of the white crystals obtained by the above reaction, 455.4 g of triethylamine, 1000 ml of chloroform were charged. Under ice cooling, 479.6 g (4.5 mol) of acryloylchloride were dissolved in 450 ml of chloroform, and the resulting solution was added dropwise to the reaction liquid from the dropping funnel while the temperature of the reaction liquid was kept below 5° C. After the completion of dropping, the reaction liquid was kept under ice cooling and stirred for two hours. Chloroform was then removed from the reaction liquid under reduced pressure, and the obtained yellow crystals were further purified by column chromatography using as a developing solvent ethyl acetate/n-hexane mixed solvent (1:4 by volume). The solvent was then removed under reduced pressure to obtain 232 g of the objective white crystal product J (yield 30%).

A portion of product J was further separated by high speed liquid chromatography in the same way as in Example 1-1. The compounds J-1 and J-2 obtained as the result of the separation were the compounds having the structures represented by the following formulae (24) and (25), respectively. The results of $^1$H-NMR, $^{19}$F-NMR, and Exact MS of the compounds thus obtained are shown below together with the structural formulae thereof.

$$CH_2=CHCOOCH_2C(CH_3)COOCH_2CHCH_2(CF_2)_8F \quad (24)$$
$$| \qquad\qquad\qquad |$$
$$CH_2=CHCOOCH_2 \qquad OCOCH=CH_2$$

(Analytical results of J-1).
$^1$H-NMR($\delta$ (ppm)CDCl$_3$/TMS): 6.43(dd,1H); 6.42(dd,2H); 6.12(dd,1H); 6.11(dd,1H); 6.10(dd,1H); 5.89(dd,2H); 5.88(dd,1H); 5.57–5.64(m,1H); 4.46,4.41(ABq,2H); 4.41,4.39(ABq,2H); 4.27,4.23(dABq,2H); 2.68–2.31(m,2H); 1.30(s,3H)

$^{19}$F-NMR($\delta$ (ppm)CDCl$_3$/CFCl$_3$):−123.10;−120.47;−119.72;−118.91; −118.60; −109.76; −77.79.

Exact MS: Measured value; 772.0969, Theoretical value; C$_{25}$H$_{21}$F$_{17}$O$_8$: 772.0965.

$$CH_2=CHCOOCH_2C(CH_3)COOCHCH_2(CF_2)_8F \quad (25)$$
$$| \qquad\qquad\qquad |$$
$$CH_2=CHCOOCH_2 \qquad CH_2OCOCH=CH_2$$

(Analytical results of J-2).
$^1$H-NMR($\delta$ (ppm)CDCl$_3$/TMS): 6.44(dd,1H); 6.42(dd,2H); 6.12(dd,1H); 6.11(dd,1H); 6.11(dd,1H); 5.89(dd,1H); 5.88(dd,2H); 5.38–5.34(m,1H); 4.43,4.36(ABq,2H); 4.41, 4.39(ABq,2H); 4.29,4.13(dABq,2H); 2.68–2.31(m,2H); 1.30(s,3H).

$^{19}$F-NMR($\delta$ (ppm)CDCl$_3$/CFCl$_3$):−123.10;−120.47;−119.71;−118.91; −118.60; −109.76; −77.78.

Exact MS: Measured value; 772.0962, Theoretical value; C$_{25}$H$_{21}$F$_{17}$O$_8$:772.0965.

Example 2-2

215 g of white crystal product K (yield 32%) was obtained in the same way as in Example 2-1 via the compounds of the structures represented by the formulae (17) and (18), except that 376.1 g (1.0 mol) of 3-perfluorohexyl-1,2-epoxypropane was employed instead of 3-perfluorooctyl-1,2-epoxypropane.

A portion of product K was separated by high speed liquid chromatography in the same way as in Example 1-1. The obtained compounds K-1 and K-2 were the compounds having the structures represented by the following formulae (26) and (27), respectively. The results of $^1$H-NMR, $^{19}$F-NMR, and Exact MS of the compounds thus obtained are shown below together with the structural formulae thereof.

$$CH_2=CHCOOCH_2C(CH_3)COOCH_2CHCH_2(CF_2)_6F \quad (26)$$
$$| \qquad\qquad\qquad |$$
$$CH_2=CHCOOCH_2 \qquad OCOCH=CH_2$$

(Analytical results of K-1).
$^1$H-NMR($\delta$ (ppm)CDCl$_3$/TMS): 6.44(dd,1H); 6.43(dd,1H); 6.42(dd,1H); 6.12(dd,1H); 6.11(dd,1H); 6.10(dd,1H); 5.89(dd,2H); 5.88(dd,1H); 5.57–5.64(m,1H); 4.47,4.41(ABq,2H); 4.41,4.39(ABq,2H); 4.28,4.23(dABq,2H); 2.68–2.31(m,2H); 1.30(s,3H).

$^{19}$F-NMR($\delta$ (ppm)CDCl$_3$/CFCl$_3$):−123.09;−120.39;−119.89;−118.89; −109.39; −77.90.

Exact MS: Measured value: 672.1023, Theoretical value: C$_{23}$H$_{21}$F$_{13}$O$_8$: 672.1029.

$$CH_2=CHCOOCH_2C(CH_3)COOCHCH_2(CF_2)_6F \quad (27)$$
$$| \qquad\qquad\qquad |$$
$$CH_2=CHCOOCH_2 \qquad CH_2OCOCH=CH_2$$

(Analytical results of K-2).
$^1$H-NMR($\delta$ (ppm)CDCl$_3$/TMS): 6.43(dd,1H); 6.42(dd,2H); 6.12(dd,1H); 6.11(dd,1H); 6.11(dd,1H); 5.88(dd,1H); 5.87(dd,2H); 5.37–5.34(m,1H); 4.43,4.36(ABq,2H); 4.41, 4.39(ABq,2H); 3.88,4.75(dABq,2H); 2.48–2.21(m,2H); 1.33(s,3H).

$^{19}$F-NMR($\delta$ (ppm)CDCl$_3$/CFCl$_3$):−123.08; −120.39;−119.88;−118.89; −109.39; −77.90.

Exact MS: Measured value: 672.1018, Theoretical value: C$_{23}$H$_{21}$F$_{13}$O$_8$: 672.1029.

Example 2-3

Product I was obtained in the same way as in Example 1-3. Into a reactor equipped with a stirrer, a thermometer, a gas introducing tube and a dropping funnel, 574 g of the product I, 151.8 g of triethylamine, and 1000 ml of chloroform were charged. Under ice cooling, 159.8 g (1.5 mol) of acryloylchloride were dissolved in 150 ml of chloroform, and the resulting solution was added dropwise to the reaction liquid from the dropping funnel while the temperature of the reaction liquid was kept below 5° C. After the completion of dropping, the reaction liquid was kept under ice cooling and stirred for two hours. Chloroform was then removed from the reaction liquid under reduced pressure, and the obtained yellow crystals were further purified by column chromatography using as a developing solvent ethyl acetate/n-hexane mixed solvent (1:4 by volume). The solvent was then removed under reduced pressure to obtain 208 g of the objective white crystal product L (yield 27%).

A portion of product L was further separated by high speed liquid chromatography in the same way as in Example 1-1. The compounds L-1 and L-2 obtained as the result of separation were the compounds having the structures represented by the formulae (24) and (25), respectively. The results of $^1$H-NMR, $^{19}$F-NMR, and Exact MS of the compounds thus obtained are shown below.

(Analytical results of L-1).

$^1$H-NMR($\delta$ (ppm)CDCl$_3$/TMS): 6.43(dd,1H); 6.42(dd, 2H); 6.12(dd,1H); 6.11(dd,1H); 6.10(dd,1H); 5.89(dd,2H); 5.88(dd,1H); 5.57–5.64(m,1H); 4.46,4.41(ABq,2H); 4.41, 4.39(ABq,2H); 4.27,4.23(dABq,2H); 2.68–2.31(m,2H); 1.30(s,3H).

$^{19}$F-NMR($\delta$ (ppm)CDCl$_3$/CFCl$_3$):−123.10;−120.47;−119.72;−118.91; −118.60; −109.76; −77.79.

Exact MS: Measured value: 772.0969, Theoretical value: C$_{25}$H$_{21}$F$_{17}$O$_8$: 772.0965.

(Analytical results of L-2).

$^1$H-NMR($\delta$ (ppm)CDCl$_3$/TMS): 6.44(dd,1H); 6.42(dd, 2H); 6.12(dd,1H); 6.11(dd,1H); 6.11(dd,1H); 5.89(dd,1H); 5.88(dd,2H); 5.38–5.34(m,1H); 4.43,4.36(ABq,2H); 4.41, 4.39(ABq,2H); 4.29,4.13(dABq,2H); 2.68–2.31(m,2H); 1.30(s,3H).

$^{19}$F-NMR($\delta$ (ppm)CDCl$_3$/CFCl$_3$):−123.10;−120.47;−119.71;−118.91; −118.60; −109.76; −77.78.

Exact MS: Measured value: 772.0962, Theoretical value: C$_{25}$H$_{21}$F$_{17}$O$_8$: 772.0965.

Synthesis Example 1

Into a reactor equipped with a stirrer, a cooling tube, and a gas introducing tube, 500 parts by weight of 30% silica sol (trade name "XBA-ST", manufactured by NISSAN CHEMICAL INDUSTRIES CO., LTD.), 100 parts by weight of 3-acryloxypropyltrimethoxysilane as a silane coupling agent (trade name "KBM-5103", manufactured by TOSHIBA SILICONE CO.) and 20 parts by weight of water were charged, gradually heated up to 100° C. in an oil bath, and stirred at this temperature for 2 hours. The cooling tube was then removed and the mixture was stirred for two hours at the oil bath temperature of 120° C., and then cooled down to the room temperature, for obtaining the reaction liquid M. It is believed that, in the reaction liquid M, the silane coupling agent modified a part of the surface of colloidal silica. A portion of the reaction liquid M was put on a Schale, and dried at 120° C. for two hours, and the weight before and after the drying was measured for measuring the solid content, which was found to be 44.6%.

Preparation Example 1

45 parts by weight of dipentaerythritol hexaacrylate manufactured by HITACHI CHEMICAL CO., LTD., 30 parts by weight of polyethylene glycol diacrylate (trade name "A-400", manufactured by SHIN-NAKAMURA CHEMICAL CO., LTD.), 4 parts by weight of "IRGACURE 184" (trade name, manufactured by CIBA GEIGY LTD.) as a curing initiator, and 20 parts by weight of isopropyl alcohol as a solvent were mixed together, and the obtained mixture was applied to a PET film by a micro gravure coater manufactured by YASUISEIKI CO., LTD. so that the film thickness was 5 $\mu$m. The film was cured by irradiating the film with ultraviolet ray by an ultraviolet irradiator manufactured by IWASAKI ELECTRIC CO., LTD. at 800 mJ/cm$^2$ to form a hard coating, thereby preparing a PET film with hard coating (abbreviated as HC-PET hereinbelow).

Preparation Example 2

A hard coating was formed on a TAC film in the same way as in Preparation Example 1 to prepare a TAC film with hard coating (abbreviated as HC-TAC hereinbelow). Next, 240 parts by weight of toluene dispersion containing 30% zinc oxide powders (trade name "ZN-300", manufactured by SUMITOMO OSAKA CEMENT CO. LTD.), 28 parts by weight of trimethylolpropane triacrylate (abbreviated as TMPTA hereinbelow), 1 part by weight of "DAROCUR1116" (trade name, manufactured by E. MELCK CORPORATION, acetophenone compound) (abbreviated as "DAROCUR1116" hereinbelow) as a curing initiator, and 1900 parts by weight of toluene as a solvent were mixed together to prepare a coating liquid. Subsequently, the coating liquid was applied to the HC-TAC by dip coating method (at pull-up rate of 100 mm/min.). The applied coating liquid was cured by irradiating with ultraviolet ray by an ultraviolet irradiator at 1000 mJ/cm$^2$ to form a layer of a high refractivity material, thereby preparing a TAC film with a layer of the high refractivity material (abbreviated as HR-TAC-A hereinbelow).

Preparation Example 3

A TAC film with a layer of the high refractivity material (abbreviated as HR-TAC-B hereinbelow) was prepared in the same way as in Preparation Example 2 except that the dip coating was carried out at the pull-out rate of 130 mm/min.

Examples 4-1 and 4-2

Product G synthesized in Example 1-1 and tetramethylolmethane tetraacrylate (abbreviated as TMMTA hereinbelow) were mixed at the mixing ratio set forth in Table 1 to prepare compositions. Each of the compositions was mixed with 400 parts by weight of trifluoromethylbenzene to prepare two kinds of coating liquids. Then, each of the coating liquids was applied to HC-PET prepared in Preparation Example 1 with the micro gravure coater. The applied coating liquids were irradiated with electron beam of the absorbed dose of 15 Mrad by an electron beam irradiator (manufactured by IWASAKI ELECTRIC CO., LTD.) at the accelerating voltage of 125 kV and the beam current of 35 mA to cure the applied compositions, thereby preparing reflection reducing PET films with a layer of the low refractivity material. The film thickness of the low refractivity material was adjusted with an instantaneous multi optical measurement system so that the wave length which indicated the minimum refractivity was 550 to 600 nm. For evaluation, the films thus obtained were subjected to the measurements of (a), (b), and (c), and the coating liquids thus obtained were subjected to the measurement of (d), each specified below.

(a) Spectral Reflectance

The spectral reflectance of the film was measured by an UV Spectrophotometer equipped with 5 degree specular reflectivity measuring attachment (manufactured by JAPAN SPECTROSCOPIC CO., LTD., trade name "U-best 35"). The measurement was effected on the coated surface, and the opposite surface of the film was roughened with a sandpaper for inhibiting reflection on the opposite surface.

Figure 2:
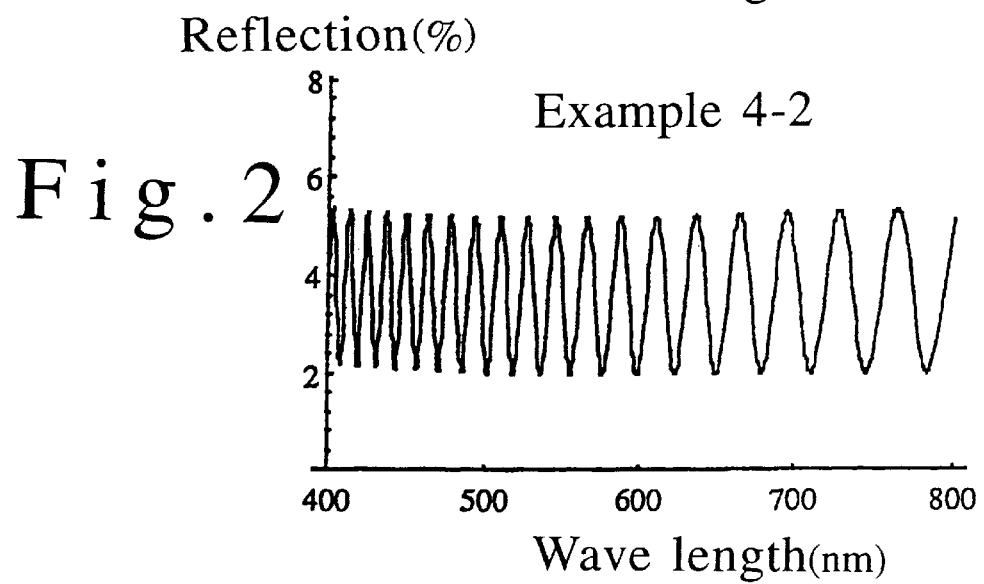
FIG. 2 is a graph showing the results of the measurements of the spectral reflectance in Example 4-2.

The results are shown in FIGS. 1 and 2. The minimum reflectance of each film is shown in Table 1.

(b) Abrasion Resistance

The scratch resistance against #0000 steel wool was measured, and evaluated according to the evaluation standard below. The results are shown in Table 1.

A: No abrasion by vigorous rubbing
B: Slight abrasion by vigorous rubbing
C: Slight abrasion by soft rubbing
D: Remarkable abrasion by soft rubbing (c) Adhesion Cross cut test was conducted in accordance with JIS K 5400. The results are shown in Table 1.

(d) Refractive Index of the Low Refractivity Material

The coating liquid was applied on a glass plate so that the dry thickness of the resulting coating film was 500 μm, and cured by irradiating with electron beam of the absorbed dose of 5 Mrad by an electron beam irradiator at the accelerating voltage of 175 kV and the beam current of 5 mA. The film thus obtained was peeled off of the glass plate, and the refractive index of the film was measured using Abbe's refractometer (manufactured by ATAGO CO., LTD.). The results are shown in Table 1.

Examples 4-3 and 4-4

Figure 3:
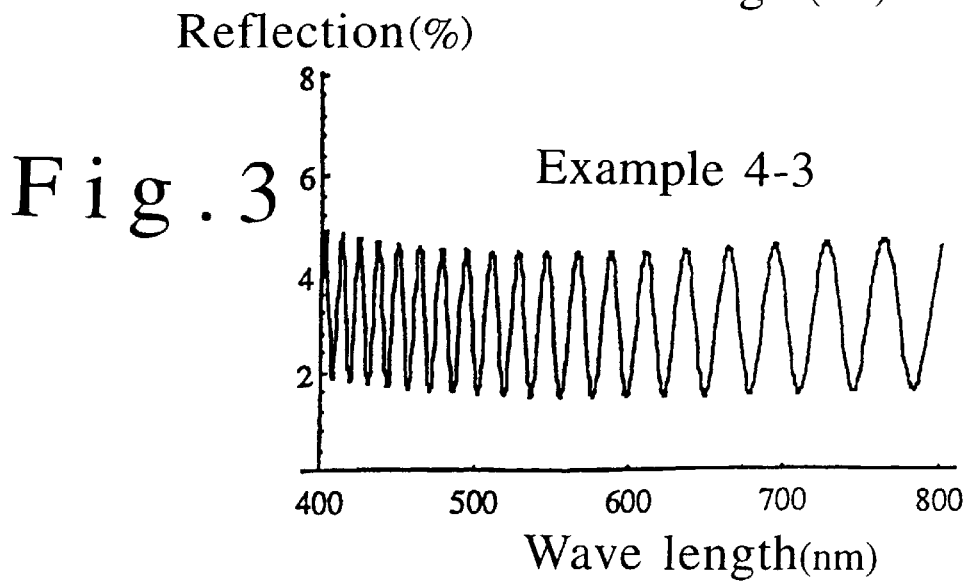
FIG. 3 is a graph showing the results of the measurements of the spectral reflectance in Example 4-3.
Figure 4:
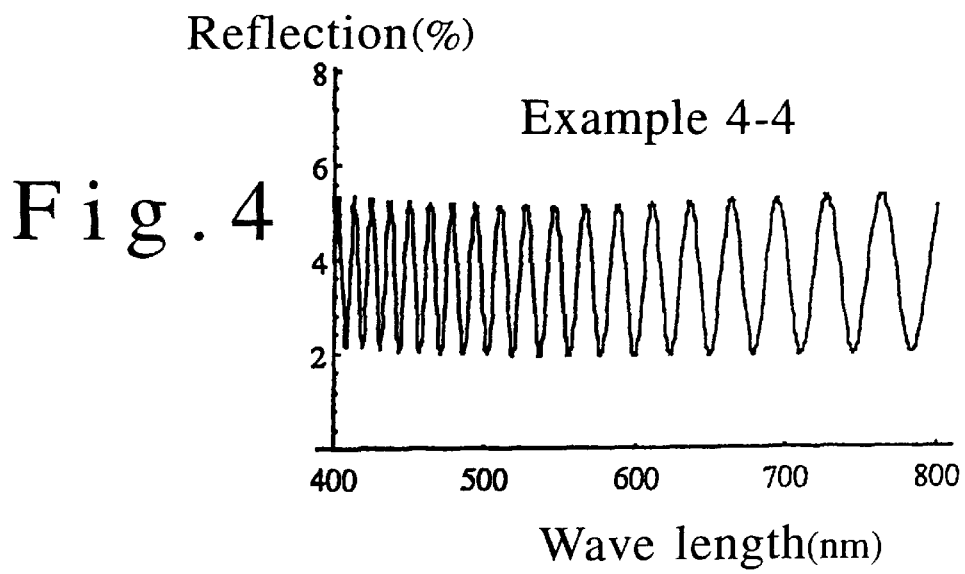
FIG. 4 is a graph showing the results of the measurements of the spectral reflectance in Example 4-4.

Product H synthesized in Example 1-2 and TMMTA were mixed together at the mixing ratio set forth in Table 1 to prepare compositions. Each of the compositions was mixed with 400 parts by weight of trifluoromethylbenzene as a solvent to prepare two kinds of coating liquids. Then, each of the coating liquids was applied to HC-PET prepared in Preparation Example 1 with the micro gravure coater. The applied coating liquids were irradiated with electron beam of the absorbed dose of 15 Mrad by the electron beam irradiator to cure the applied compositions, thereby preparing reflection reducing PET films with a layer of the low refractivity material. The film thickness of the low refractivity material was adjusted in the same way as in Examples 4-1 and 4-2. The coating liquids and the reflection reducing films thus obtained were subjected to the same evaluation tests for spectral reflectance, minimum reflection, adhesion, abrasion resistance and refractive index as in Examples 4-1 and 4-2. The results are shown in FIGS. 3 and 4 and Table 1.

Examples 4-5 and 4-6

Figure 5:
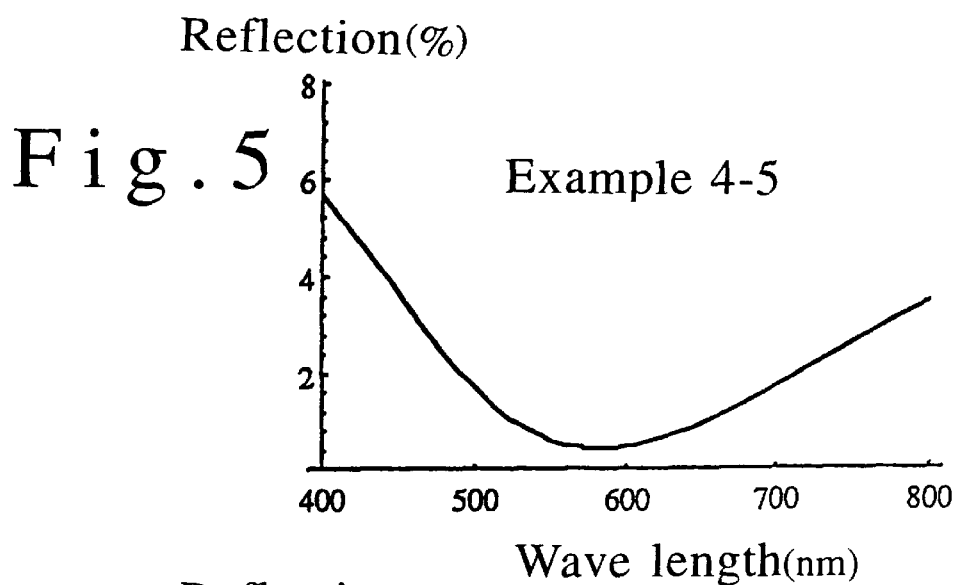
FIG. 5 is a graph showing the results of the measurements of the spectral reflectance in Example 4-5.
Figure 6:
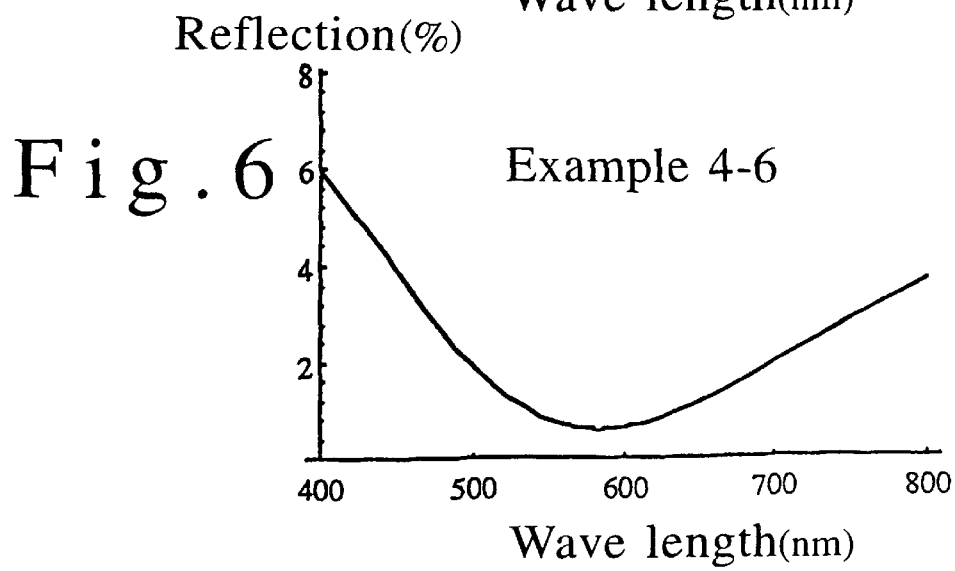
FIG. 6 is a graph showing the results of the measurements of the spectral reflectance in Example 4-6.

Product G, TMMTA, 10% magnesium fluoride sol (trade name "MFS-10P" manufacture by NISSAN CHEMICAL INDUSTRIES CO., LTD.; referred to hereinbelow as "MFS-10P"), and DAROCUR 1116 were mixed together at the mixing ratio set forth in Table 1 to prepare compositions. Each of the compositions was mixed with 400 parts by weight of trifluoromethylbenzene as a solvent to prepare two kinds of coating liquids. Then, each of the coating liquids was applied to HR-TAC-A prepared in Preparation Example 2 with the micro gravure coater. The applied coating liquids were irradiated three times with ultraviolet ray by an ultraviolet irradiator at 1000 mJ/cm$^2$ to cure the applied compositions, thereby preparing reflection reducing TAC films with laminated layers of the low refractivity material and the high refractivity material. The film thickness of the low refractivity material was adjusted in the same way as in Examples 4-1 and 4-2. The coating liquids and the reflection reducing films thus obtained were subjected to the same evaluation tests for spectral reflectance, minimum reflection, adhesion, abrasion resistance, and refractive index as in Examples 4-1 and 4-2. The results are shown in FIGS. 5 and 6 and Table 1.

Examples 4-7 and 4-8

Figure 7:
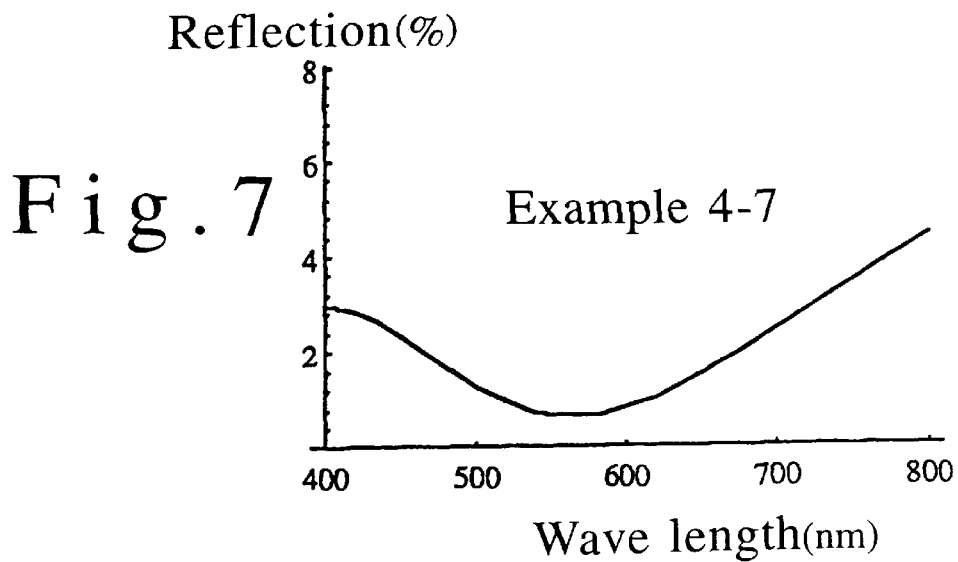
FIG. 7 is a graph showing the results of the measurements of the spectral reflectance in Example 4-7.
Figure 8:
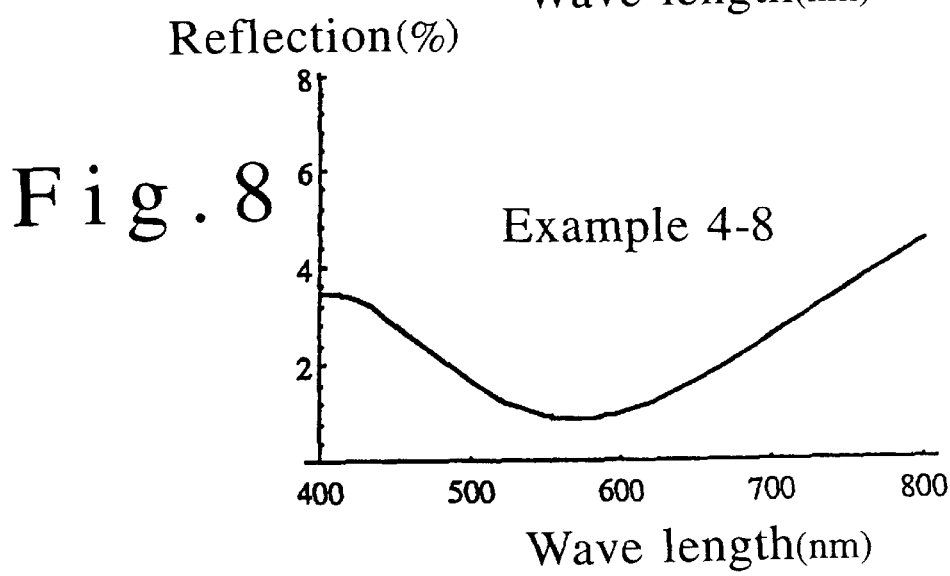
FIG. 8 is a graph showing the results of the measurements of the spectral reflectance in Example 4-8.

Product G, 4,4,5,5,6,6,7,7-octafluorodecan- 1,2,9,10-tetraol tetraacrylate (abbreviated as $F_8DTA$ hereinbelow), the reaction liquid M and DAROCUR 1116 were mixed together at the mixing ratio set forth in Table 1 to prepare compositions. Each of the compositions was mixed with 400 parts by weight of trifluoromethylbenzene as a solvent to prepare two kinds of coating liquids. Then, each of the coating liquids was applied to HR-TAC-B prepared in Preparation Example 3 with the micro gravure coater. The applied coating liquids were irradiated three times with ultraviolet ray by an ultraviolet irradiator at 1000 mJ/cm$^2$ to cure the applied compositions, thereby preparing reflection reducing TAC films with laminated layers of the low refractivity material and the high refractivity material. The film thickness of the low refractivity material was adjusted in the same way as in Examples 4-1 and 4-2. The coating liquids and the reflection reducing films thus obtained were subjected to the same evaluation tests for spectral reflectance, minimum reflection, adhesion, abrasion resistance, and refractive index as in Examples 4-1 and 4-2. The results are shown in FIGS. 7 and 8 and Table 1.

Comparative Examples 1 and 2

Figure 9:
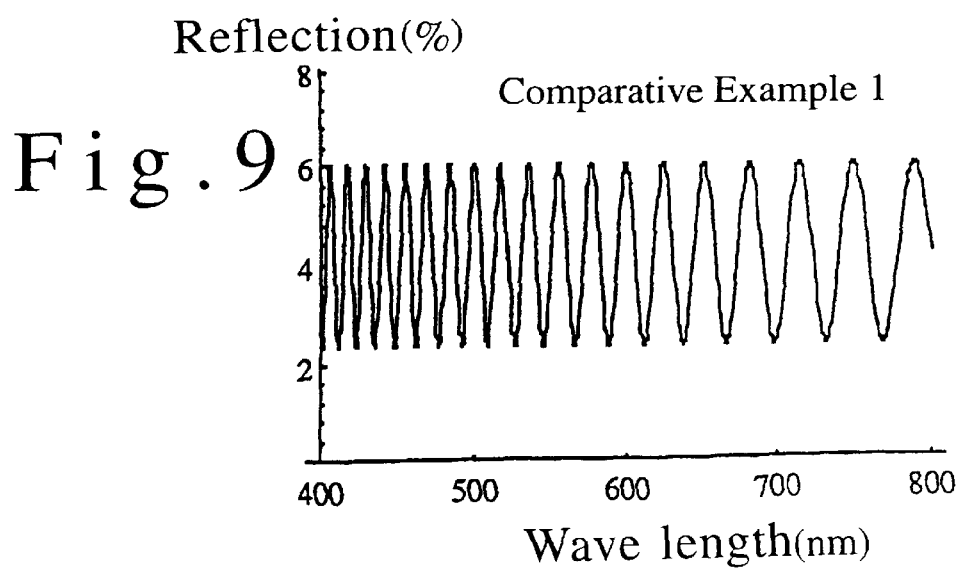
FIG. 9 is a graph showing the results of the measurements of the spectral reflectance in Comparative Example 1.
Figure 10:
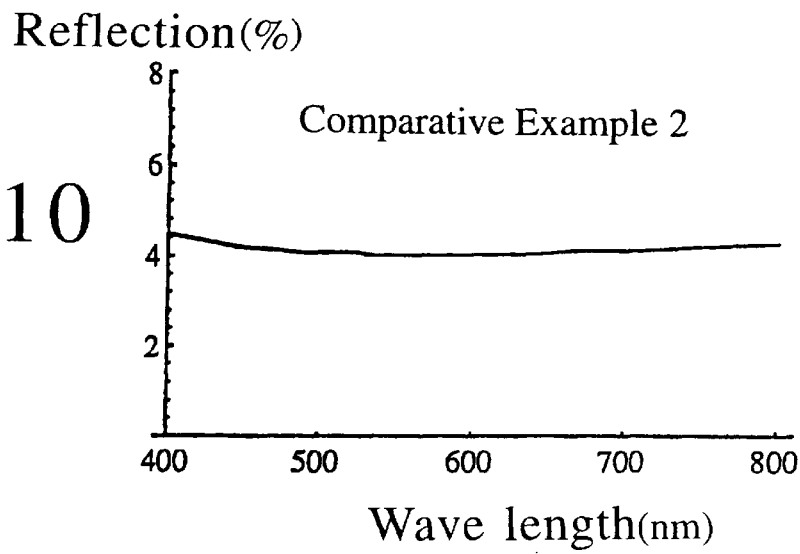
FIG. 10 is a graph showing the results of the measurements of the spectral reflectance in Comparative Example 2.

The spectral reflectance, the minimum reflection, and the abrasion resistance of HC-PET and HC-TAC prepared in Preparation Examples 1 and 2, respectively, were measured in the same way as in Examples 4-1 and 4-2. The results are shown in FIGS. 9 and 10 and Table 1.

Comparative Example 3

Figure 11:
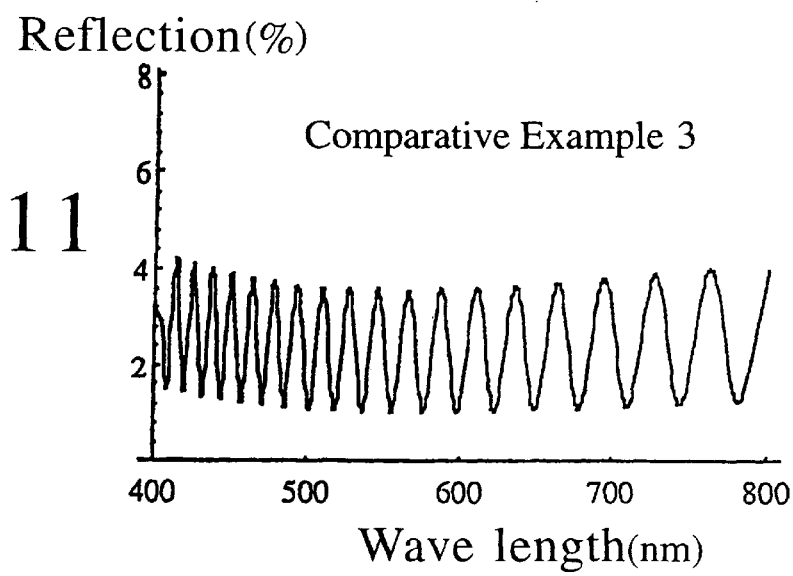
FIG. 11 is a graph showing the results of the measurements of the spectral reflectance in Comparative Example 3.

2,2,3,3,4,4,5,5,6,6,7,7,8,8,9,9,9-heptadecafluorononylethylene glycol diacrylate (abbreviated as $F_{17}EDA$ hereinbelow) and TMMTA were mixed at the mixing ratio set forth in Table 1, and further mixed with 400 parts by weight of trifluoromethylbenzene as a solvent to prepare a coating liquid. Then the coating liquid thus obtained was applied to HC-PET prepared in Preparation Example 1 with the micro gravure coater. The applied coating liquid was irradiated with electron beam of the absorbed dose of 15 Mrad by the electron beam irradiator at the accelerating voltage of 125 kV and the beam current of 35 mA to cure the applied coating liquid, thereby preparing a reflection reducing PET film with a layer of the low refractivity material. The film thickness of the low refractivity material was adjusted in the same way as in Examples 4-1 and 4-2. The coating liquid and the reflection reducing film thus obtained were subjected to the same evaluation tests for spectral reflectance, minimum reflection, adhesion, abrasion resistance and refractive index, as in Examples 4-1 and 4-2. The results are shown in FIG. 11 and Table 1.

Comparative Example 4

Figure 12:
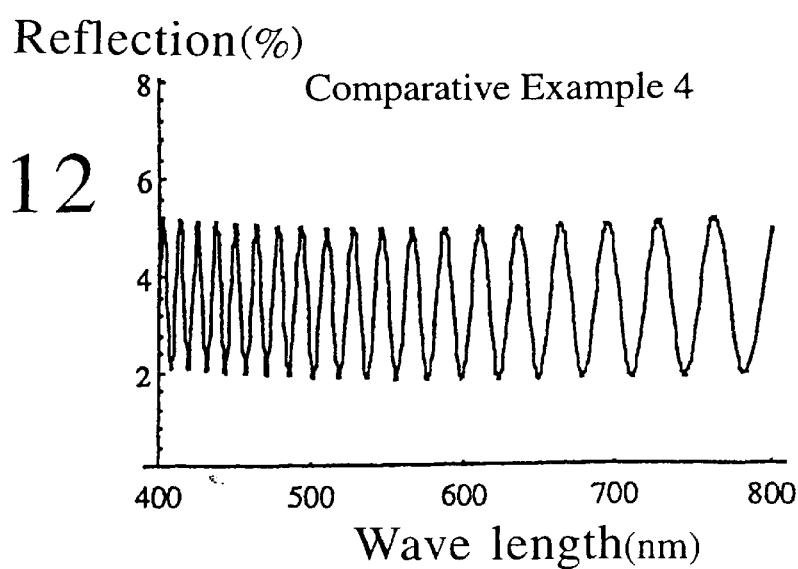
FIG. 12 is a graph showing the results of the measurements of the spectral reflectance in Comparative Example 4.

$F_8DTA$ and TMMTA were mixed at the mixing ratio set forth in Table 1, and further mixed with 400 parts by weight of trifluoromethylbenzene as a solvent to prepare a coating liquid. Then, the coating liquid was applied to HC-PET prepared in Preparation Example 1 with the micro gravure coater. The applied coating liquid was irradiated with electron beam of the absorbed dose of 15 Mrad by the electron beam irradiator at the accelerating voltage of 125 kV and beam current of 35 mA to cure the applied mixture, thereby preparing a reflection reducing PET film with a layer of the low refractivity material. The film thickness of the low refractivity material was adjusted in the same way as in Examples 4-1 and 4-2. The coating liquid and the reflection reducing film thus obtained were subjected to the same evaluation tests for spectral reflectance, minimum reflection, adhesion, abrasion resistance and refractive index as in Examples 4-1 and 4-2. The results are shown in FIG. 12 and Table 1.

(manufactured by IWASAKI ELECTRIC CO., LTD.) at the accelerating voltage of 125 kV and the beam current of 35 mA to cure the applied compositions, thereby preparing reflection reducing PET films with a layer of the low refractivity material. The film thickness of the low refractivity material was adjusted in the same way as in Examples

TABLE 1

| | Substrate film | Fulorine-containing bifunctional monomer containing OH group | | Fluorine-containing monomer | | Poly-functional monomer | Inorganic powders | | Curing initiator | Minimum reflection | Adhesion | Scratch resistance | Refractive index |
|---|---|---|---|---|---|---|---|---|---|---|---|---|---|
| | | Product G parts by weight | Product H parts by weight | tetra-functional $F_8DTA$ parts by weight | bi-functional $F_{17}EDA$ parts by weight | TMMTA parts by weight | MFS-10P parts by weight | Reaction liquid M parts by weight | D.1116 parts by weight | | | | |
| Ex. 4-1 | HC-PET | 70 | — | — | — | 30 | — | — | — | 1.5 | 100/100 | C | 1.446 |
| Ex. 4-2 | HC-PET | 30 | — | — | — | 70 | — | — | — | 2.0 | 100/100 | B | 1.474 |
| Ex. 4-3 | HC-PET | — | 70 | — | — | 30 | — | — | — | 1.5 | 100/100 | C | 1.448 |
| Ex. 4-4 | HC-PET | — | 40 | — | — | 60 | — | — | — | 2.0 | 100/100 | B | 1.472 |
| Ex. 4-5 | HR-TAC-A | 20 | — | — | — | 80 | 30 | — | 1 | 0.5 | 100/100 | B | 1.447 |
| Ex. 4-6 | HR-TAC-A | 25 | — | — | — | 85 | 15 | — | 1 | 0.6 | 100/100 | A | 1.465 |
| Ex. 4-7 | HR-TAC-B | 50 | — | 20 | — | — | — | 60 | 1 | 0.7 | 100/100 | B | 1.446 |
| Ex. 4-8 | HR-TAC-B | 10 | — | 50 | — | — | — | 80 | 1 | 0.9 | 100/100 | A | 1.446 |
| Comp. Ex. 1 | HC-PET | — | — | — | — | — | — | — | — | 2.4 | — | A | — |
| Comp. Ex. 2 | HC-TAC | — | — | — | — | — | — | — | — | 4.0 | — | A | — |
| Comp. Ex. 3 | HC-PET | — | — | — | 70 | 30 | — | — | — | 1.1 | 30/100 | D | 1.421 |
| Comp. Ex. 4 | HC-PET | — | — | 70 | — | 30 | — | — | — | 1.8 | 40/100 | A | 1.467 |

Examples 5-1 and 5-2

Figure 13:
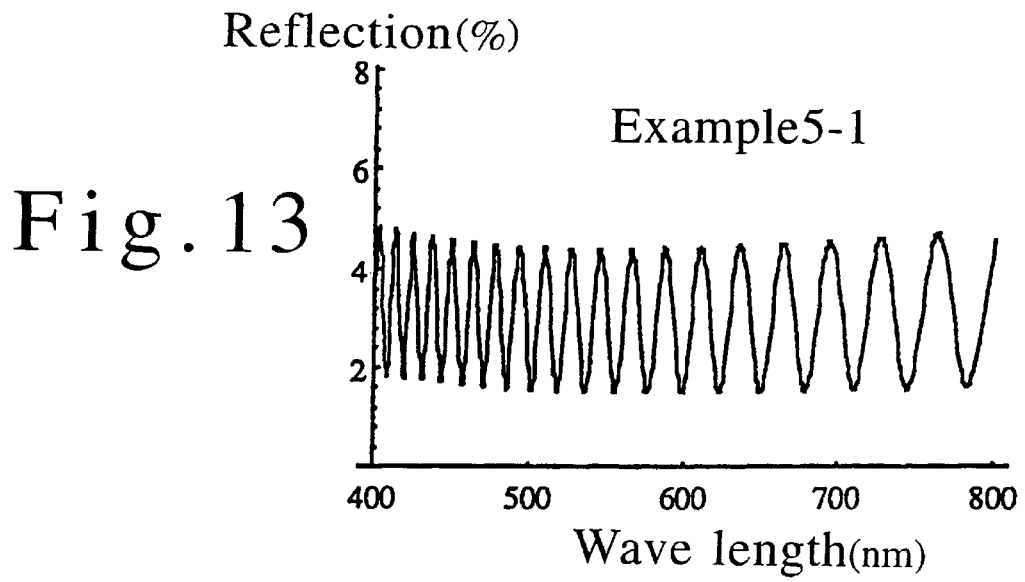
FIG. 13 is a graph showing the results of the measurements of the spectral reflectance in Example 5-1.
Figure 14:
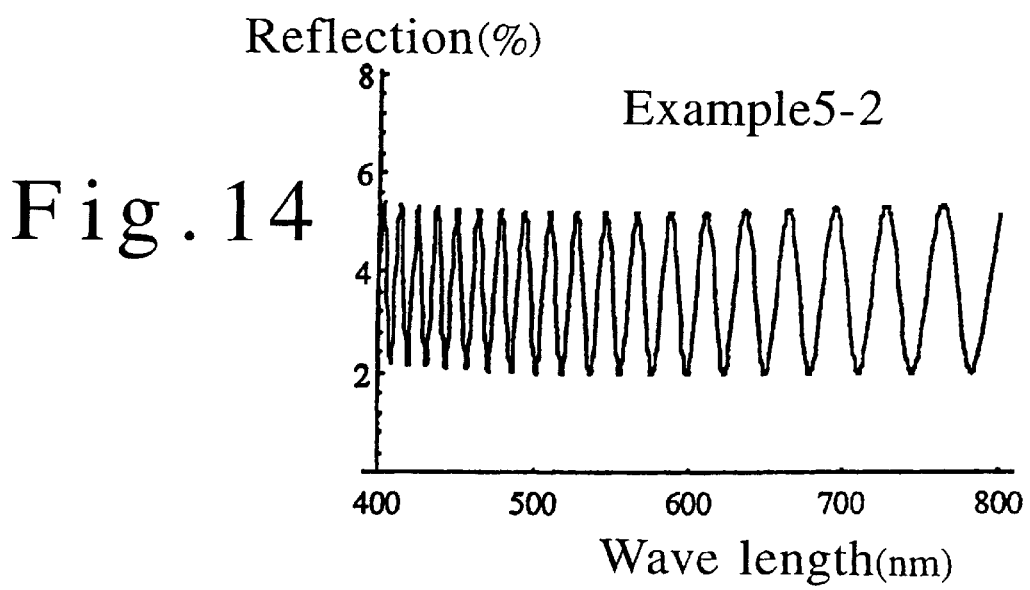
FIG. 14 is a graph showing the results of the measurements of the spectral reflectance in Example 5-2.

Product J synthesized in Example 2-1 and TMMTA were mixed at the mixing ratio set forth in Table 2 to prepare compositions. Each of the compositions was mixed with 400 parts by weight of trifluoromethylbenzene to prepare two kinds of coating liquids. Then, each of the coating liquids was applied to HC-PET prepared in Preparation Example 1 with the micro gravure coater. The applied coating liquids were irradiated with electron beam of the absorbed dose of 15 Mrad by an electron beam irradiator (manufactured by IWASAKI ELECTRIC CO., LTD.) at the accelerating voltage of 125 kV and the beam current of 35 mA to cure the applied compositions, thereby preparing reflection reducing PET films with a layer of the low refractivity material. The film thickness of the low refractivity material was adjusted in the same way as in Examples 4-1 and 4-2. The coating liquids and the reflection reducing films thus obtained were subjected to the same evaluation tests for spectral reflectance, minimum reflection, abrasion resistance and refractive index as in Examples 4-1 and 4-2. The results are shown in FIGS. 13 and 14 and Table 2.

Examples 5-3 and 5-4

Figure 15:
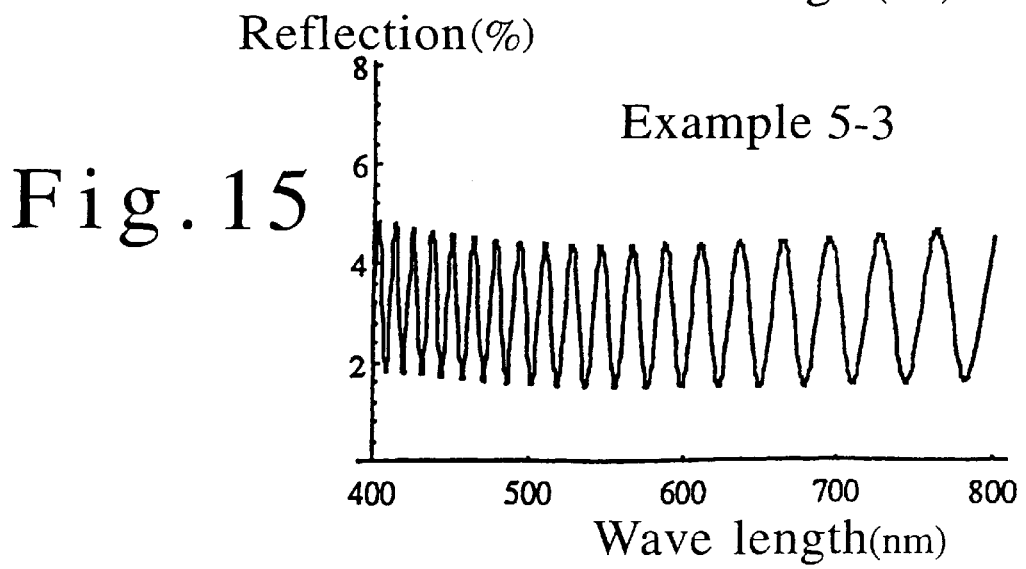
FIG. 15 is a graph showing the results of the measurements of the spectral reflectance in Example 5-3.
Figure 16:
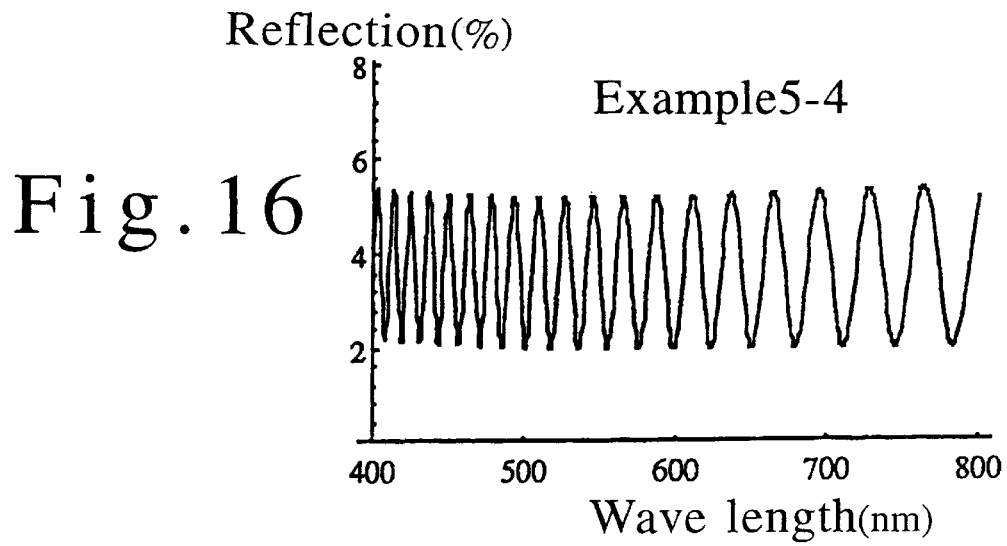
FIG. 16 is a graph showing the results of the measurements of the spectral reflectance in Example 5-4.

Product K synthesized in Example 2-2 and TMMTA were mixed together at the mixing ratio set forth in Table 2 to prepare compositions. Each of the compositions was mixed with 400 parts by weight of trifluoromethylbenzene as a solvent to prepare two kinds of coating liquids. Then, each of the coating liquids was applied to HC-PET prepared in Preparation Example 1 with the micro gravure coater. The applied coating liquids were irradiated with electron beam of the absorbed dose of 15 Mrad by an electron beam irradiator (manufactured by IWASAKI ELECTRIC CO., LTD.) at the accelerating voltage of 125 kV and the beam current of 35 mA to cure the applied compositions, thereby preparing reflection reducing PET films with a layer of the low refractivity material. The film thickness of the low refractivity material was adjusted in the same way as in Examples 4-1 and 4-2. The coating liquids and the reflection reducing films thus obtained were subjected to the same evaluation tests for spectral reflectance, minimum reflection, abrasion resistance and refractive index as in Examples 4-1 and 4-2. The results are shown in FIGS. 15 and 16 and Table 2.

Examples 5-5 and 5-6

Figure 17:
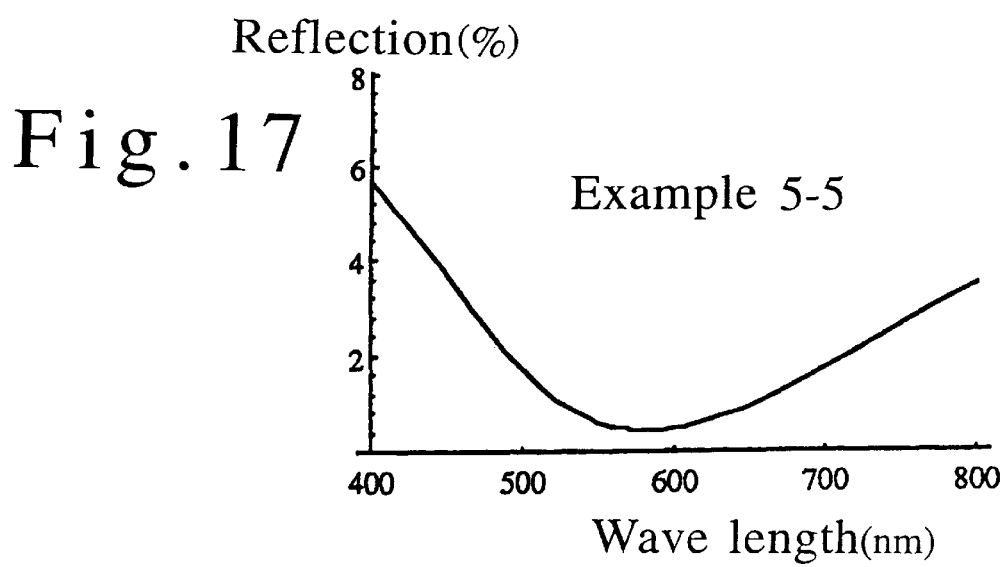
FIG. 17 is a graph showing the results of the measurements of the spectral reflectance in Example 5-5.
Figure 18:
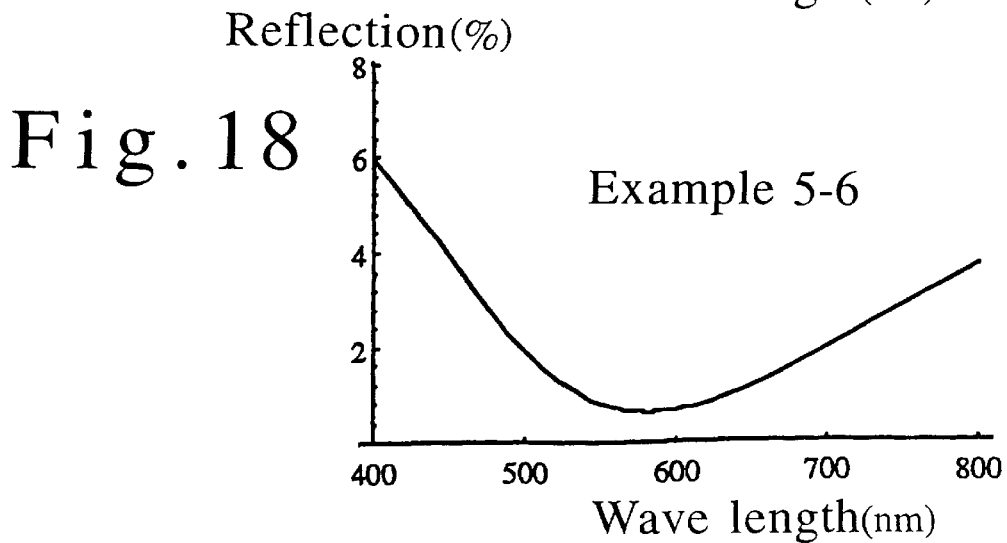
FIG. 18 is a graph showing the results of the measurements of the spectral reflectance in Example 5-6.

Product J, TMMTA, MFS-10P and DOROCUR 1116 were mixed together at the mixing ratio set forth in Table 2 to prepare compositions. Each of the compositions was mixed with 400 parts by weight of trifluoromethylbenzene as a solvent to prepare two kinds of coating liquids. Then, each of the coating liquids was applied to HR-TAC-A prepared in Preparation Example 2 with the micro gravure coater. Each of the applied coating liquids was irradiated three times with ultraviolet ray by an ultraviolet irradiator at 1000 mJ/cm$^2$ to cure the coating liquid, thereby preparing reflection reducing films with a layer of the low refractivity material. The film thickness of the low refractivity material was adjusted in the same way as in Examples 4-1 and 4-2. The coating liquids and the reflection reducing films thus obtained were subjected to the same evaluation tests for spectral reflectance, minimum reflection, abrasion resistance and refractive index as in Examples 4-1 and 4-2. The results are shown in FIGS. 17 and 18 and Table 2.

Examples 5-7 and 5-8

Product J, TMMTA, reaction liquid M and DOROCUR 1116 were mixed together at the mixing ratio set forth in Table 2 to prepare compositions. Each of the compositions was mixed with 400 parts by weight of trifluoromethylbenzene as a solvent to prepare two kinds of coating liquids.

Figure 19:
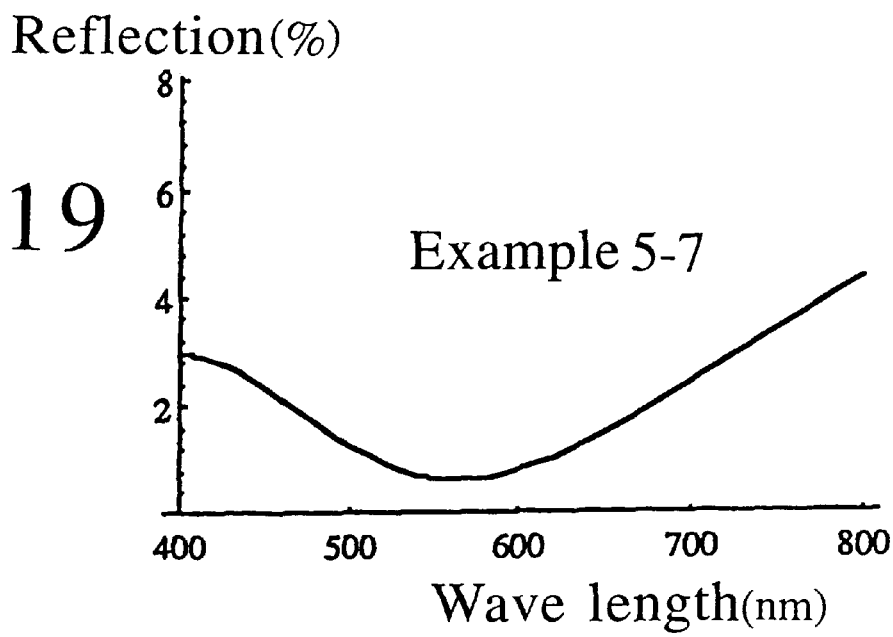
FIG. 19 is a graph showing the results of the measurements of the spectral reflectance in Example 5-7.
Figure 20:
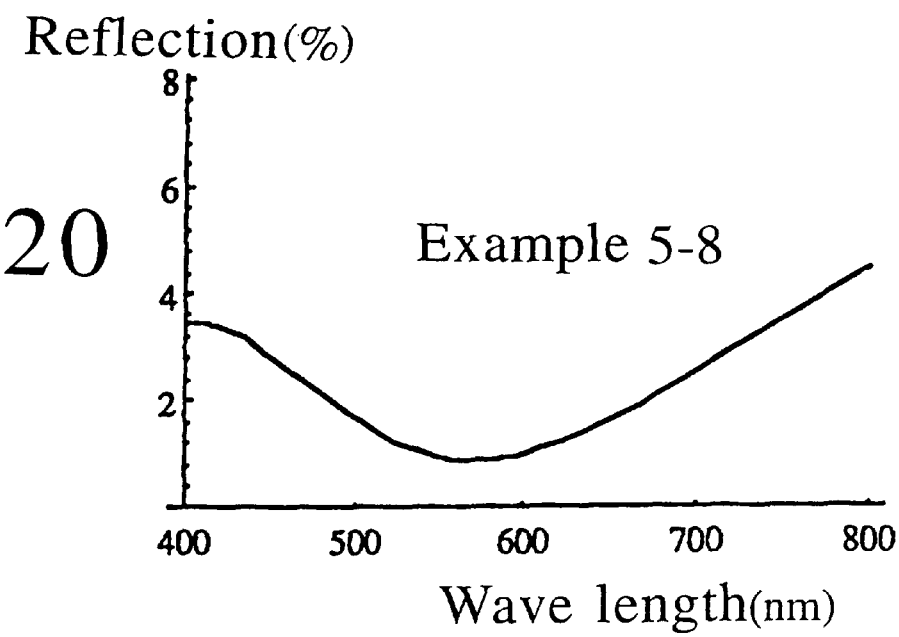
FIG. 20 is a graph showing the results of the measurements of the spectral reflectance in Example 5-8.

Then, each of the coating liquids was applied to HR-TAC-B prepared in Preparation Example 3 with the micro gravure coater. Each of the applied coating liquids was irradiated three times with ultraviolet ray by an ultraviolet irradiator at 1000 mJ/cm² to cure the coating liquid, thereby preparing reflection reducing films with a layer of the low refractivity material. The film thickness of the low refractivity material was adjusted in the same way as in Examples 4-1 and 4-2. The coating liquids and the reflection reducing films thus obtained were subjected to the same evaluation tests for spectral reflectance, minimum reflection, abrasion resistance and refractive index as in Examples 4-1 and 4-2. The results are shown in FIGS. 19 and 20 and Table 2.

Comparative Example 5

Figure 21:
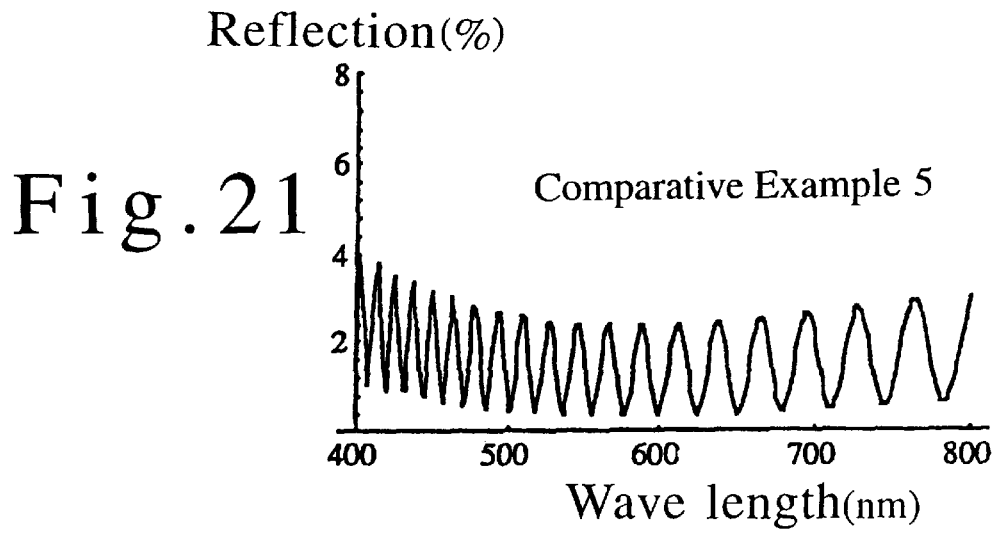
FIG. 21 is a graph showing the results of the measurements of the spectral reflectance in Comparative Example 5.

100 parts by weight of heptadecafluorodecyl acrylate (abbreviated as $F_{17}A$ hereinbelow) and 400 parts by weight of trifluoromethylbenzene as a solvent were mixed together to prepare a coating liquid. Then, the coating liquid was applied to HC-PET prepared in Preparation Example 1 with the micro gravure coater. The applied coating liquid was irradiated with electron beam of the absorbed dose of 15 Mrad by an electron beam irradiator (manufactured by IWASAKI ELECTRIC CO., LTD.) at the accelerating voltage of 125 kV and the beam current of 35 mA to cure the applied composition, thereby preparing a reflection reducing PET film with a layer of the low refractivity material. The film thickness of the low refractivity material was adjusted in the same way as in the Examples 4-1 and 4-2. The coating liquid and the reflection reducing film thus obtained were subjected to the same evaluation tests for spectral reflectance, minimum reflection, abrasion resistance and refractive index as in Examples 4-1 and 4-2. The results are shown in FIG. 21 and Table 2.

Comparative Examples 6 and 7

Figure 22:
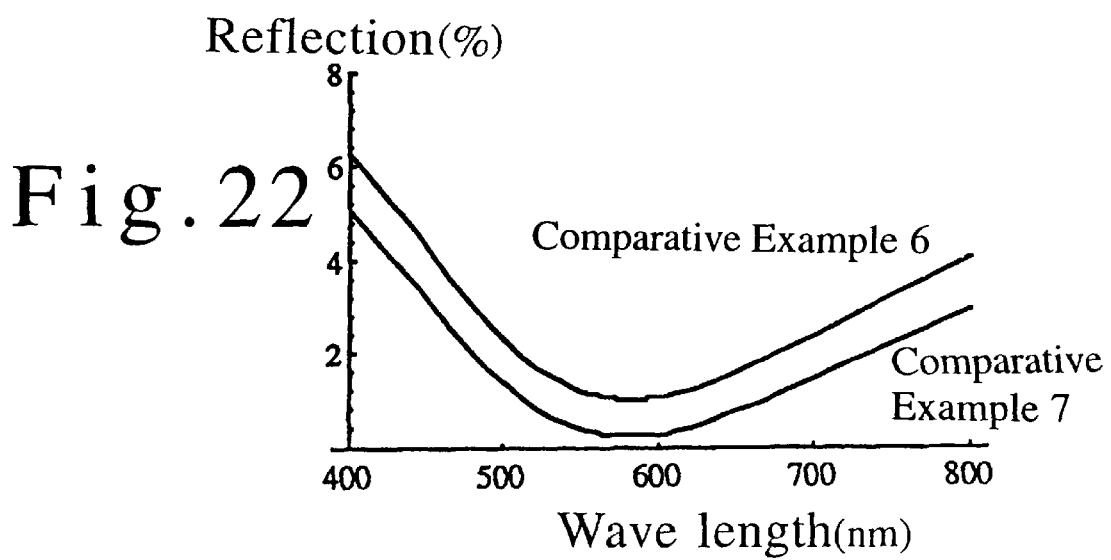
FIG. 22 is a graph showing the results of the measurements of the spectral reflectance in Comparative Examples 6 and 7.

100 parts by weight of either $F_{17}EDA$ or TMMTA was mixed with 400 parts by weight of trifluoromethylbenzene as a solvent to prepare two kinds of coating liquids. Each of the coating liquids was applied to HR-TAC-A prepared in Preparation Example 3 with the micro gravure coater. Each of the applied coating liquids was irradiated three times with ultraviolet ray by an ultraviolet irradiator at 1000 mJ/cm² to cure the coating liquid, thereby preparing reflection reducing films with a layer of the low refractivity material. The film thickness of the low refractivity material was adjusted in the same way as in Examples 4-1 and 4-2. The coating liquids and the reflection reducing films thus obtained were subjected to the same evaluation tests for spectral reflectance, minimum reflection, abrasion resistance and refractive index as in Examples 4-1 and 4-2. The results are shown in FIGS. 22 and Table 2.

Comparative Examples 8 to 10

$F_{17}EDA$ and TMMTA were mixed at the mixing ration set forth in Table 2. However, none of these were compatible and became turbid in white.

TABLE 2

| | Substrate film | Fluorine-containing trifunctional monomer | | Fluorine-containing monomer | | Poly-functional monomer | Inorganic powders | | Curing initiator | Minimum reflection | Scratch resistance | Refractive index |
| | | Product J parts by weight | Product K parts by weight | tetra-functional $F_{17}A$ parts by weight | bi-functional $F_{17}EDA$ parts by weight | TMMTA parts by weight | MFS-10P parts by weight | Reaction liquid M parts by weight | D.1116 parts by weight | | | |
|---|---|---|---|---|---|---|---|---|---|---|---|---|
| Ex. 5-1 | HC-PET | 70 | — | — | — | 30 | — | — | — | 1.5 | C | 1.447 |
| Ex. 5-2 | HC-PET | 30 | — | — | — | 70 | — | — | — | 1.9 | B | 1.473 |
| Ex. 5-3 | HC-PET | — | 70 | — | — | 30 | — | — | — | 1.5 | C | 1.447 |
| Ex. 5-4 | HC-PET | — | 30 | — | — | 70 | — | — | — | 2.0 | B | 1.483 |
| Ex. 5-5 | HR-TAC-A | 40 | — | — | — | 40 | 150 | — | 1 | 0.5 | B | 1.448 |
| Ex. 5-6 | HR-TAC-A | 30 | — | — | — | 50 | 100 | — | 1 | 0.6 | A | 1.464 |
| Ex. 5-7 | HR-TAC-B | 80 | — | — | — | 20 | — | 60 | 1 | 0.7 | B | 1.443 |
| Ex. 5-8 | HR-TAC-B | 40 | — | — | — | 40 | — | 80 | 1 | 0.9 | A | 1.474 |
| Comp. Ex. 5 | HC-PET | — | — | 100 | — | — | — | — | — | 0.4 | D | 1.364 |
| Comp. Ex. 6 | HR-TAC-A | — | — | — | — | 100 | — | — | — | 1.0 | B | 1.505 |
| Comp. Ex. 7 | HR-TAC-A | — | — | — | 100 | — | — | — | — | 0.3 | D | 1.388 |
| Comp. Ex. 8 | | — | — | — | 70 | 30 | — | — | — | Not compatible | | |
| Comp. Ex. 9 | | — | — | — | 50 | 50 | — | — | — | Not compatible | | |
| Comp. Ex. 10 | | — | — | — | 30 | 70 | — | — | — | Not compatible | | |

What is claimed is:

1. Fluorine-containing polyfunctional (meth)acrylate represented by the formula (1):

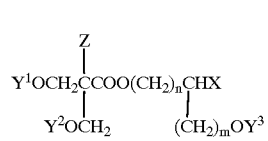

(1)

wherein X stands for a fluoroalkyl group having 1 to 14 carbon atoms and 3 or more fluorine atoms, or a fluorocycloalkyl group having 3 to 14 carbon atoms and 4 or more fluorine atoms; $Y^1$, $Y^2$, and $Y^3$ stand for a hydrogen atom, an acryloyl group or a methacryloyl group, and at least two of $Y^1$, $Y^2$, and $Y^3$ are the same or different groups and stand for an acryloyl group or a methacryloyl group; Z stands for a hydrogen atom or an alkyl group having 1 to 3 carbon atoms; and n and m is an integer of 0 or 1, and n+m=1.

2. The fluorine-containing polyfunctional (meth)acrylate as claimed in claim 1 wherein n=1 and m=0 and wherein said fluorine-containing polyfunctional (meth)acrylate is selected from the group consisting of fluorine-containing bifunctional (meth)acrylate having (meth)acryloyl groups and a hydroxyl group in which two of $Y^1$, $Y^2$ and $Y^3$ stand for an acryloyl group or a methacryloyl group, and the remaining one of $Y^1$, $Y^2$ and $Y^3$ stands for a hydrogen atom; and fluorine-containing trifunctional (meth)acrylate in which $Y^1$, $Y^2$ and $Y^3$ are the same or different groups and stand for an acryloyl group or a methacryloyl group.

3. The fluorine-containing polyfunctional (meth)acrylate as claimed in claim 1 wherein n=0 and m=1 and wherein said fluorine-containing polyfunctional (meth)acrylate is selected from the group consisting of fluorine-containing bifunctional (meth)acrylate having (meth)acryloyl groups and a hydroxyl group in which two of $Y^1$, $Y^2$ and $Y^3$ stand for an acryloyl group or a methacryloyl group, and the remaining one of $Y^1$, $Y^2$ and $Y^3$ stands for a hydrogen atom; and fluorine-containing trifunctional (meth)acrylate in which $Y^1$, $Y^2$ and $Y^3$ are the same or different groups and stand for an acryloyl group or a methacryloyl group.

4. A composition comprising 5 to 100% by weight of said fluorine-containing polyfunctional (meth)acrylate as claimed in claim 1.

5. The composition as claimed in claim 4 further comprising powders of an inorganic compound.

6. A low refractivity material having refractive index of 1.49 or lower prepared by a method comprising the step of curing said composition as claimed in claim 4 or 5 by polymerization.

7. A reflection reducing film comprising a transparent substrate and a layer of said low refractivity material as claimed in claim 6.

8. The reflection reducing film as claimed in claim 7 further comprising a hard coating for improving abrasion resistance.

9. The reflection reducing film as claimed in claim 7 further comprising at least one material layer between the transparent substrate and the layer of the low refractivity material.

10. The reflection reducing film as claimed in claim 9 wherein said material layer is a layer of a high refractivity material having refractive index of 1.55 or higher.

* * * * *